(12) United States Patent
Whayne

(10) Patent No.: US 6,702,828 B2
(45) Date of Patent: Mar. 9, 2004

(54) ANASTOMOSIS SYSTEM

(75) Inventor: James G. Whayne, Chapel Hill, NC (US)

(73) Assignee: Converge Medical, Inc., Sunnyvale, CA (US)

( * ) Notice: Subject to any disclaimer, the term of this patent is extended or adjusted under 35 U.S.C. 154(b) by 202 days.

(21) Appl. No.: 09/770,560

(22) Filed: Jan. 26, 2001

(65) Prior Publication Data

US 2003/0167064 A1 Sep. 4, 2003

Related U.S. Application Data

(60) Provisional application No. 60/178,822, filed on Jan. 28, 2000, provisional application No. 60/169,104, filed on Dec. 6, 1999, and provisional application No. 60/151,863, filed on Sep. 1, 1999.

(51) Int. Cl.[7] .............................................. A61B 17/11
(52) U.S. Cl. ...................................... 606/153; 606/155
(58) Field of Search ................................ 606/153, 155, 606/156, 151, 154, 157, 213, 158, 191, 194, 139; 623/1.36

(56) References Cited

U.S. PATENT DOCUMENTS

| 5,690,674 A | * | 11/1997 | Diaz ........................... 606/213 |
| 5,713,917 A | | 2/1998 | Leonhardt et al. |
| 5,755,778 A | | 5/1998 | Kleshinski |
| 5,893,886 A | * | 4/1999 | Zegdi et al. ................. 606/153 |
| 6,004,347 A | | 12/1999 | McNamara et al. |
| 6,030,395 A | | 2/2000 | Nash et al. |
| 6,149,681 A | | 11/2000 | Houser et al. |
| 6,293,955 B1 | | 9/2001 | Houser et al. |
| 6,391,036 B1 | * | 5/2002 | Berg et al. .................. 606/151 |
| 6,458,140 B2 | * | 10/2002 | Akin et al. .................. 606/153 |
| 6,494,889 B1 | * | 12/2002 | Fleischman et al. ......... 606/155 |
| 6,565,581 B1 | * | 5/2003 | Spence et al. ............... 606/153 |
| 2002/0013591 A1 | * | 1/2002 | Fleischman et al. ......... 606/155 |
| 2002/0173809 A1 | * | 11/2002 | Fleischman et al. ......... 606/153 |
| 2003/0100920 A1 | * | 5/2003 | Akin et al. .................. 606/213 |

FOREIGN PATENT DOCUMENTS

| EP | 824 901 A2 A3 | 2/1998 |
| EP | 894 475 A1 | 2/1999 |
| WO | WO 98/19625 A2 A3 | 5/1998 |
| WO | WO 98/40036 A1 | 9/1998 |
| WO | WO 98/52474 A1 | 11/1998 |
| WO | WO 99/48427 A1 | 9/1999 |
| WO | WO 99/63910 A1 | 12/1999 |
| WO | WO 99/65409 A1 | 12/1999 |
| WO | WO 00/15144 A1 | 3/2000 |
| WO | WO 01/41653 A2 A3 | 6/2001 |

\* cited by examiner

*Primary Examiner*—A. Vanatta
(74) *Attorney, Agent, or Firm*—Carol M. LaSalle; Bozicevic, Field & Francis LLP

(57) ABSTRACT

End-side anastomosis fittings are described which may be deployed over a guidewire, in a sheath, or by feeding the fitting through an opening in a host vessel wall. When a fitting as described is deployed within a host vessel, the exterior surface of the leading petal contacts the interior surface of the host vessel. The leading petal is configured so that it is capable of dilating the host vessel wall opening while being being advanced through the opening. The fitting also includes links which define spaces throughout the leading petal. A deflectable rear petal anchors the fitting within the host vessel once it is advanced through the host vessel wall. Additional petals may be included to provide more complete contact. The fitting also includes extensions fitted around the base to improve hemostasis and the fitting itself may be inserted by a deployment sheath which may also serve as a dilator.

10 Claims, 22 Drawing Sheets

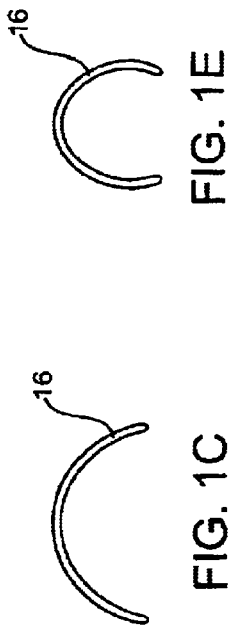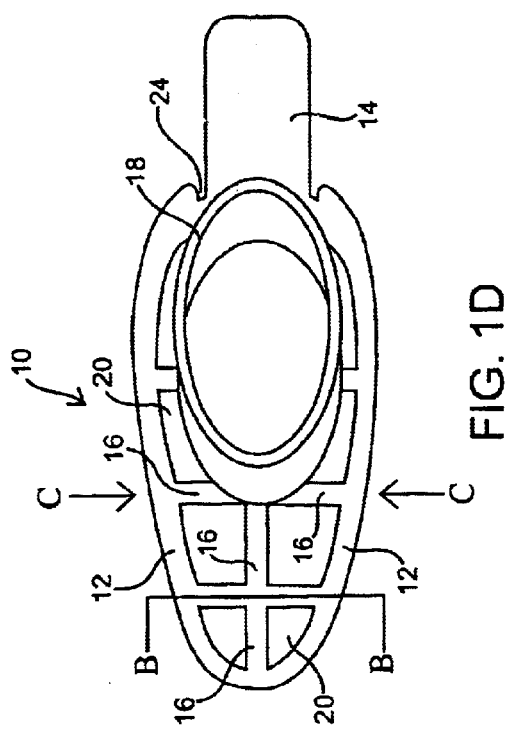
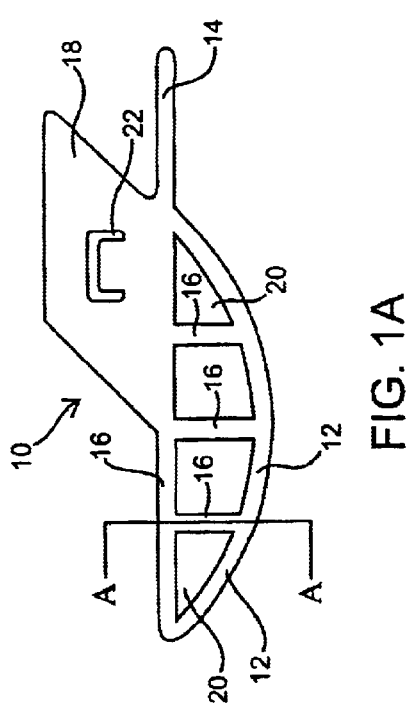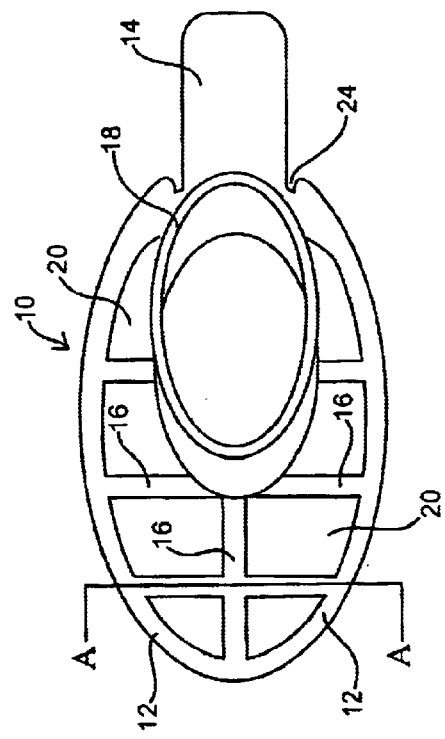

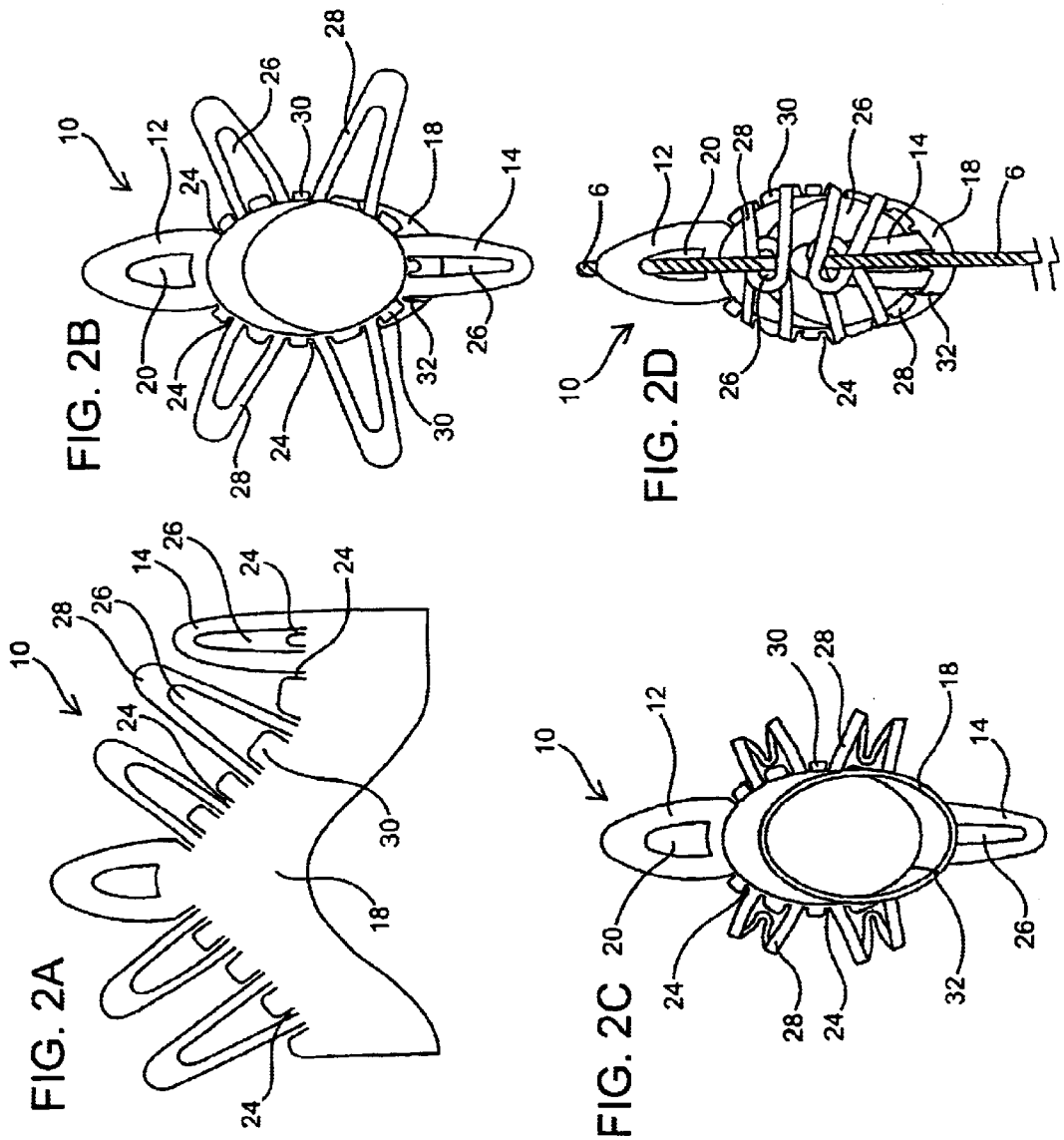

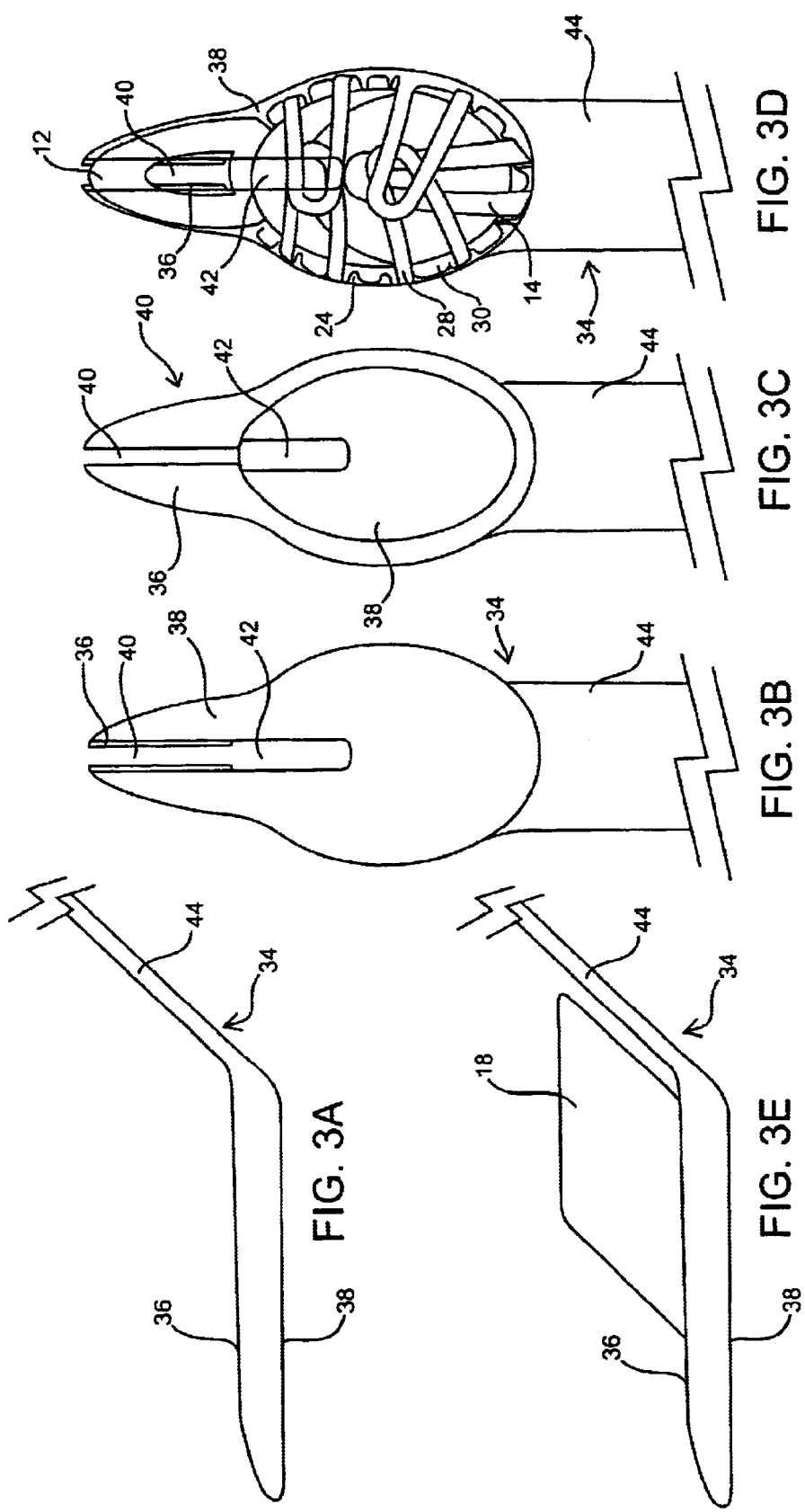

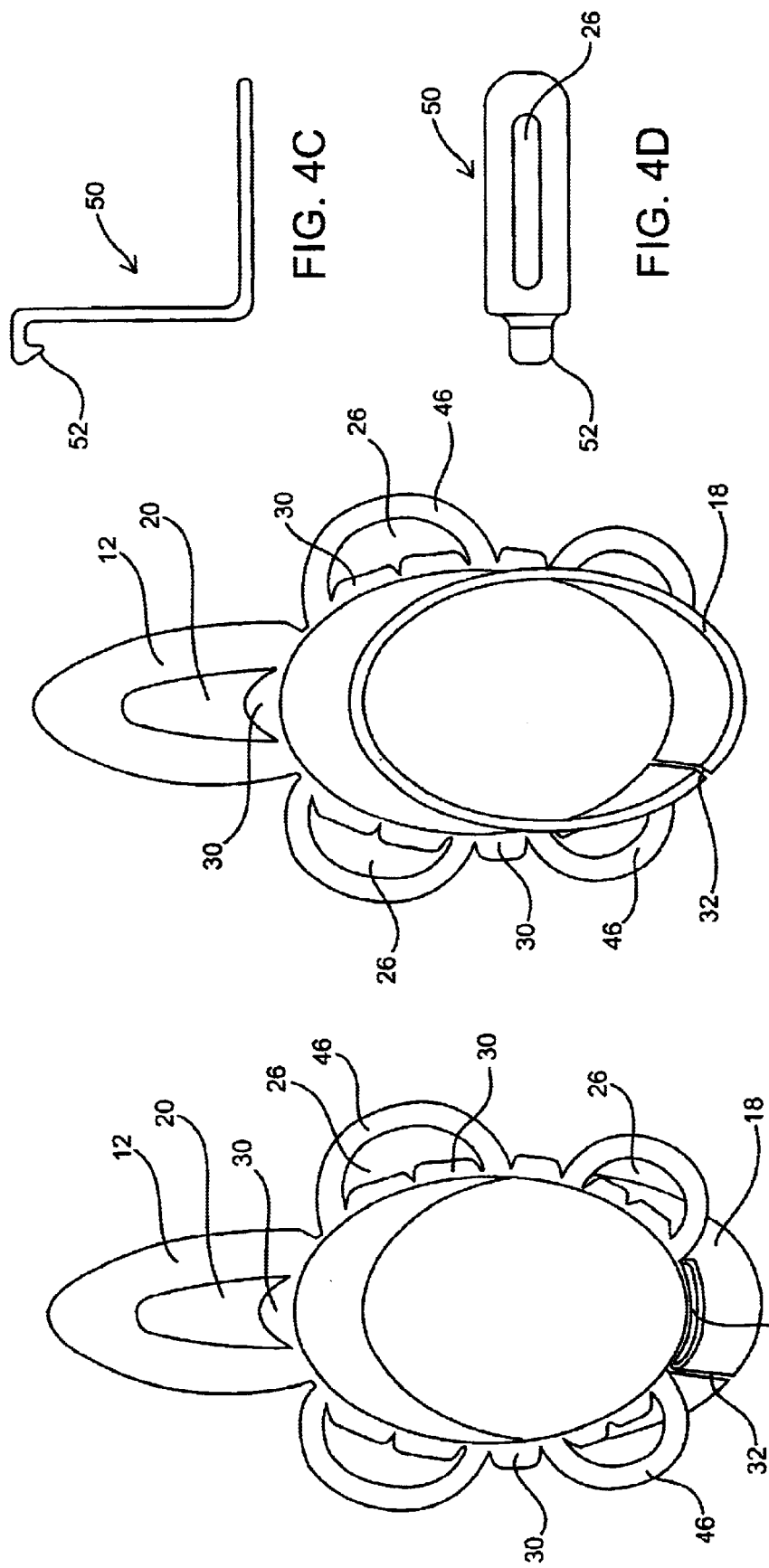

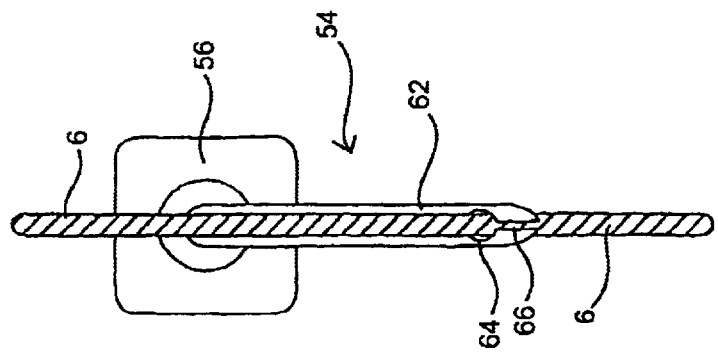
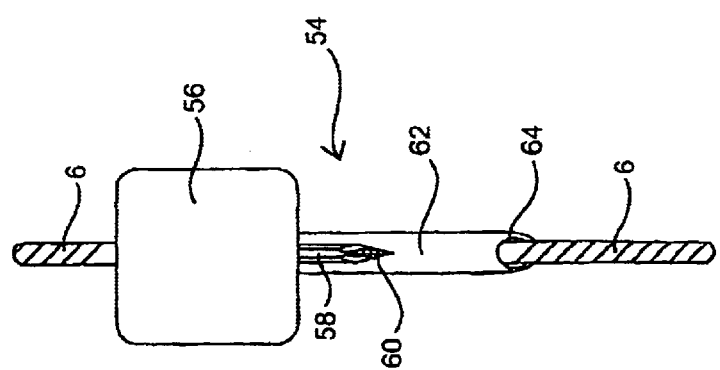
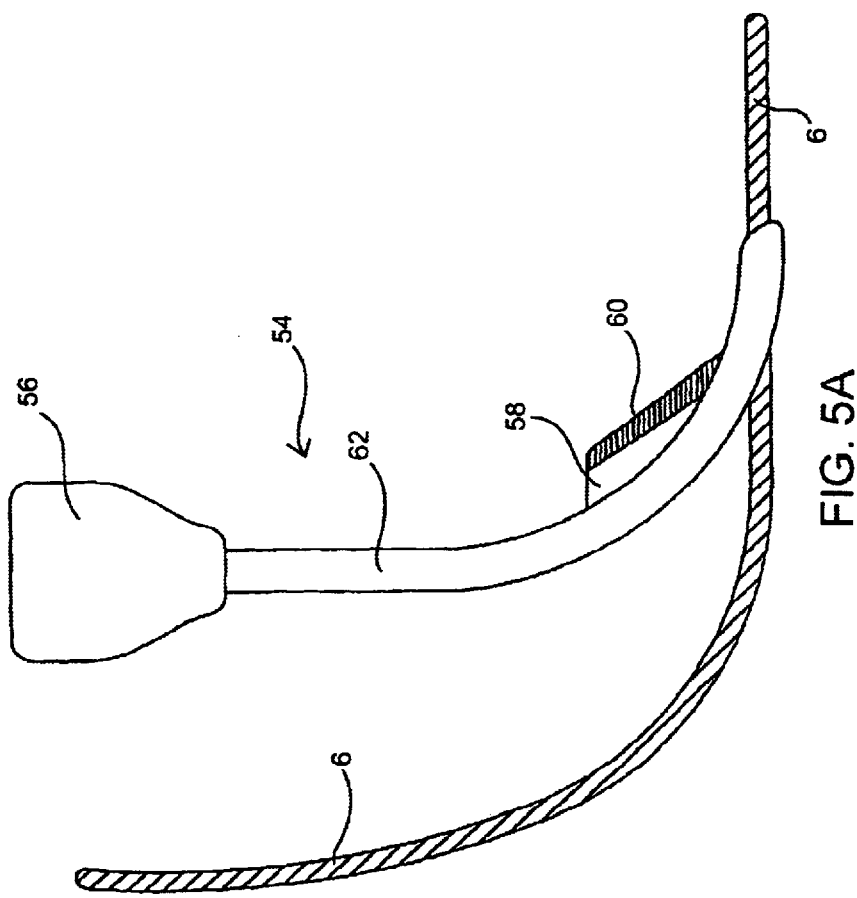

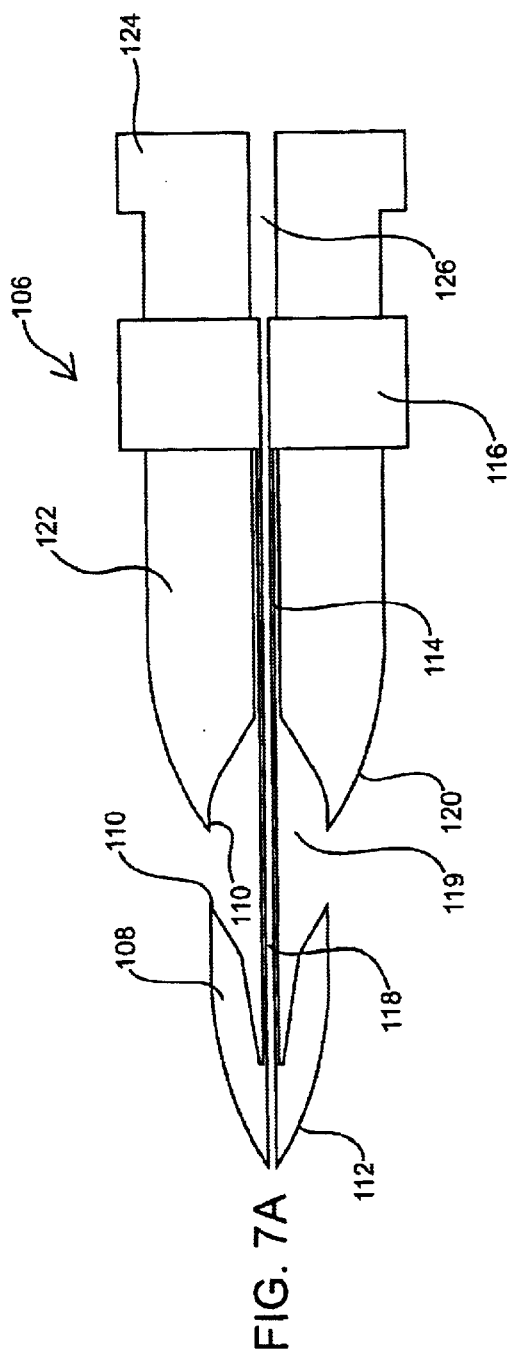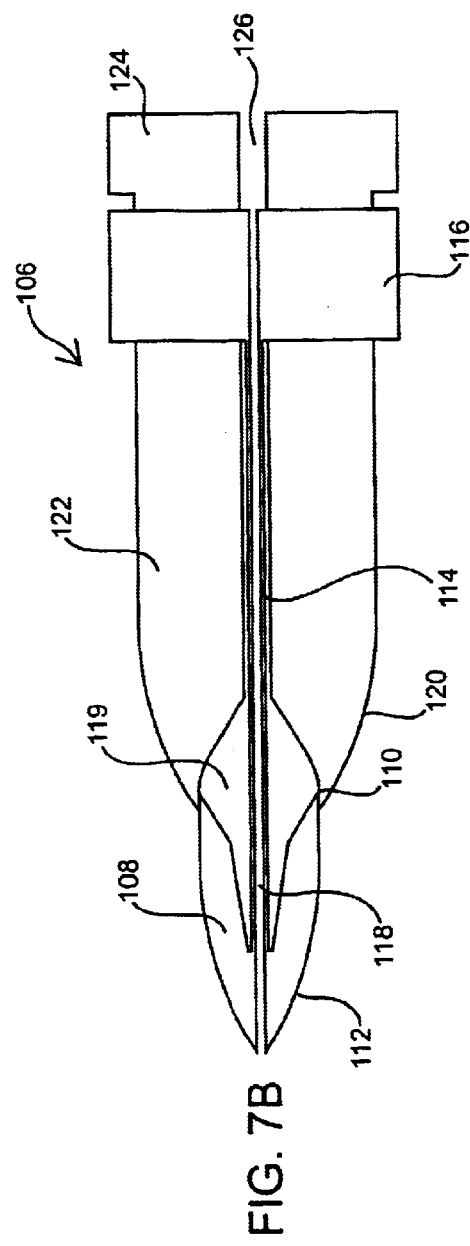

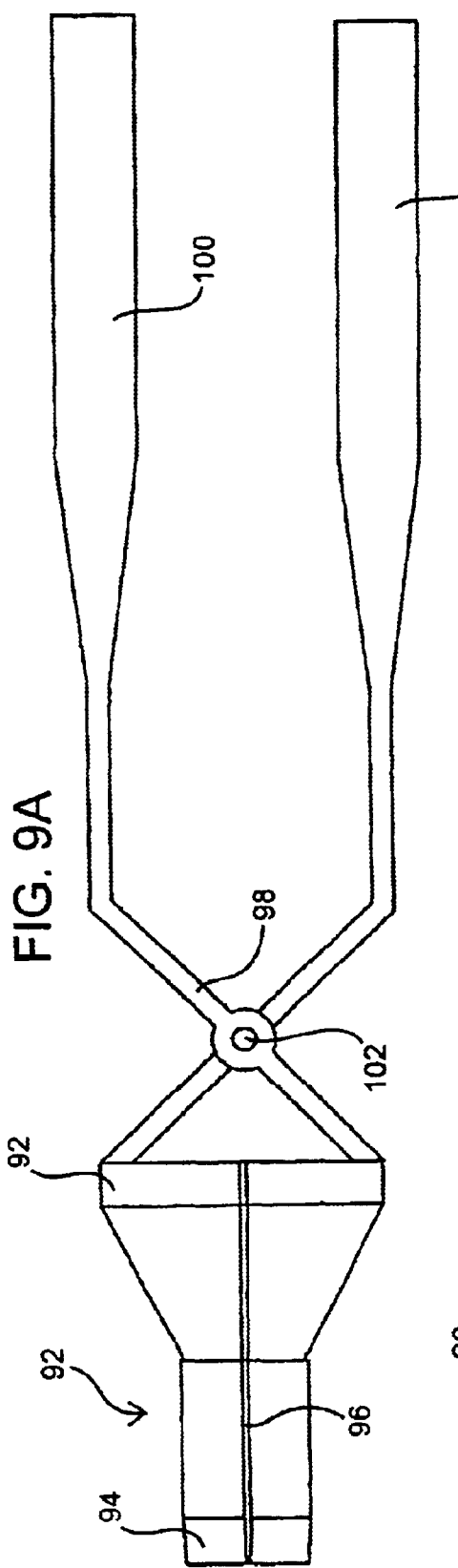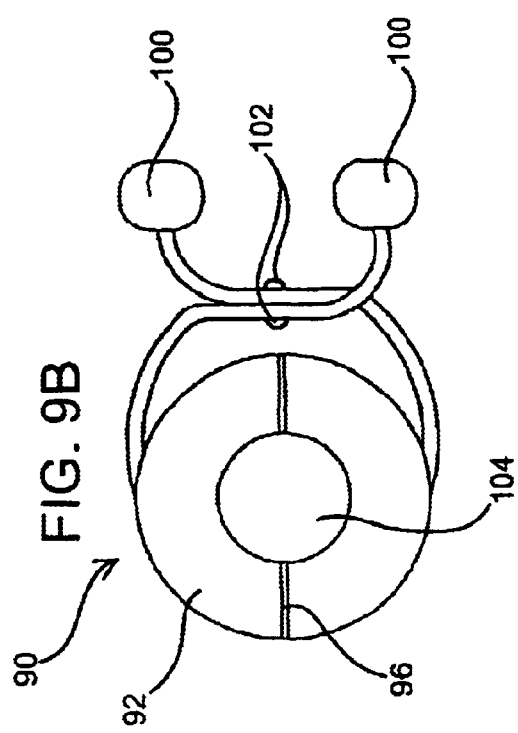

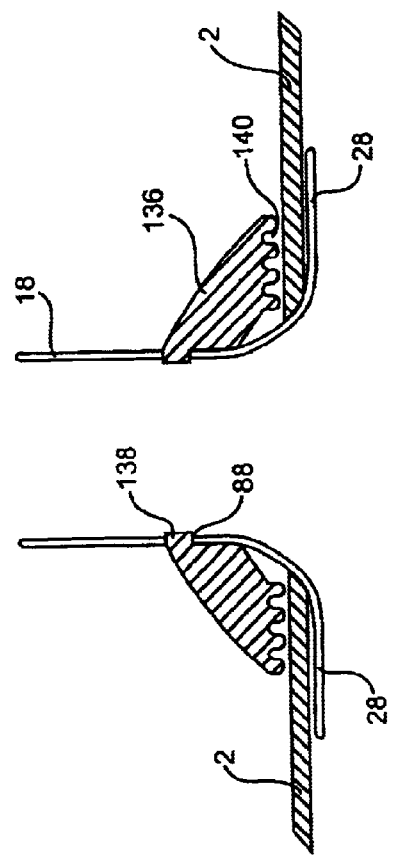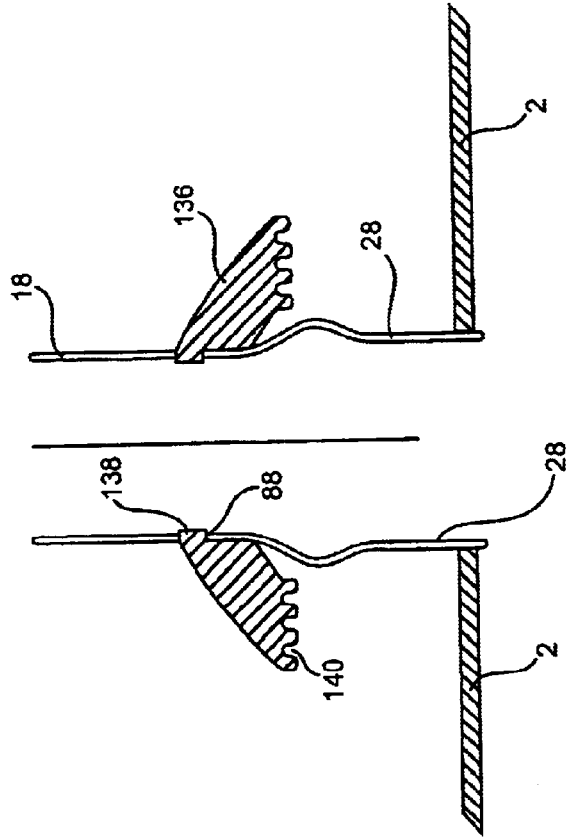
FIG. 11A
FIG. 11B

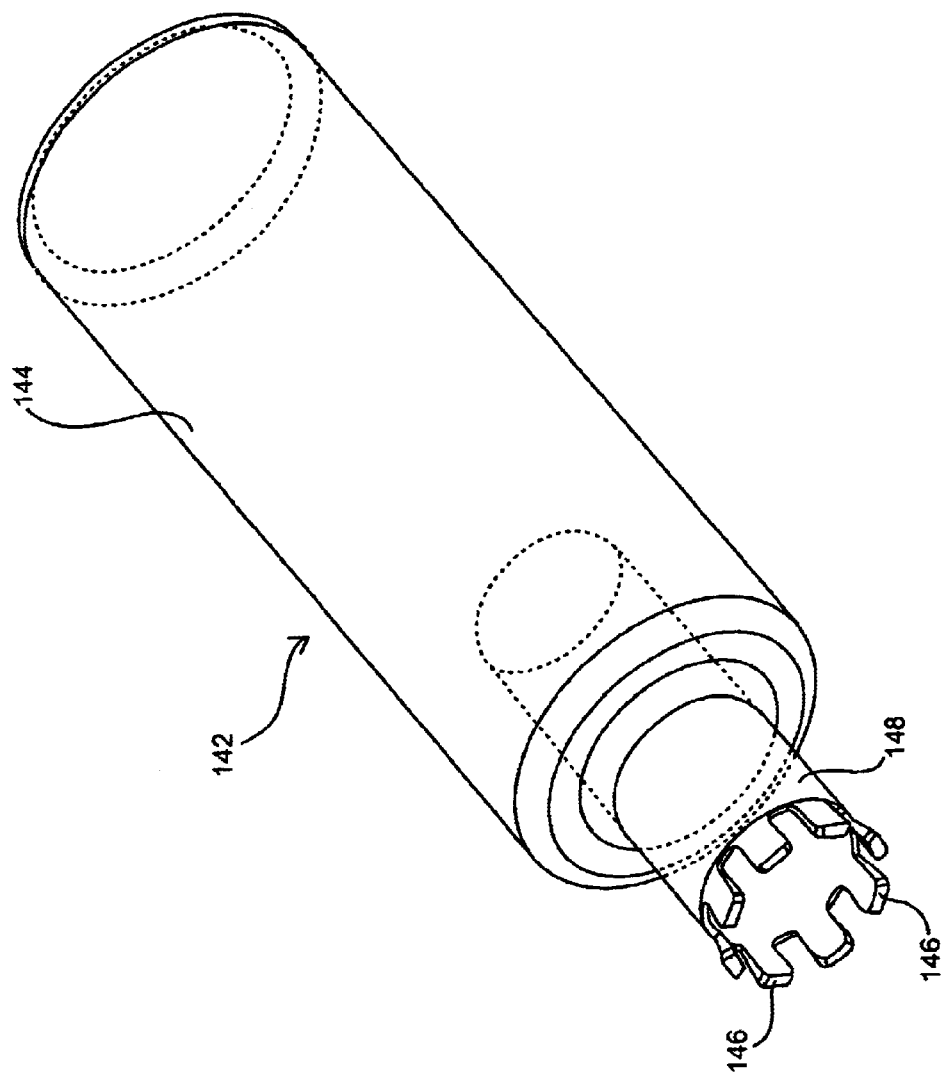

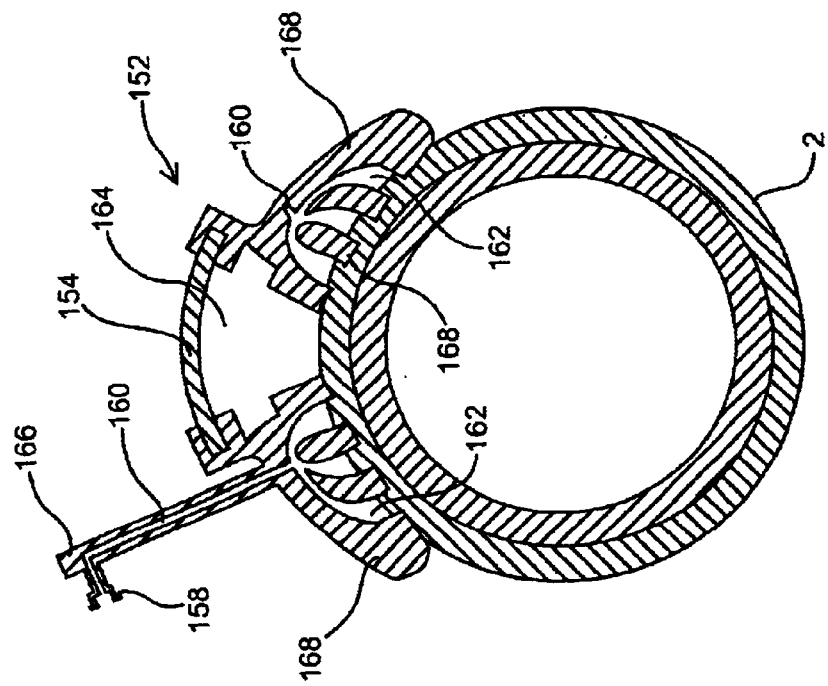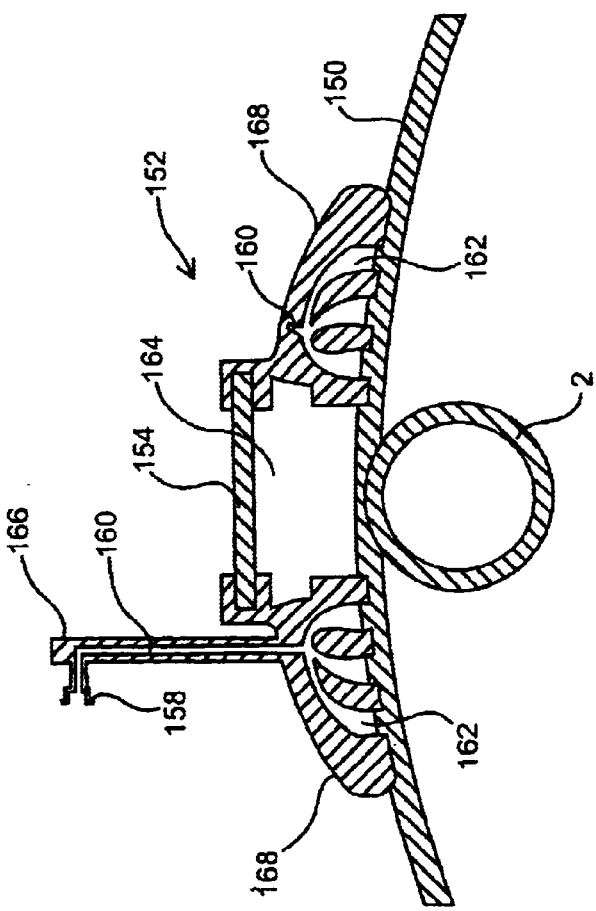

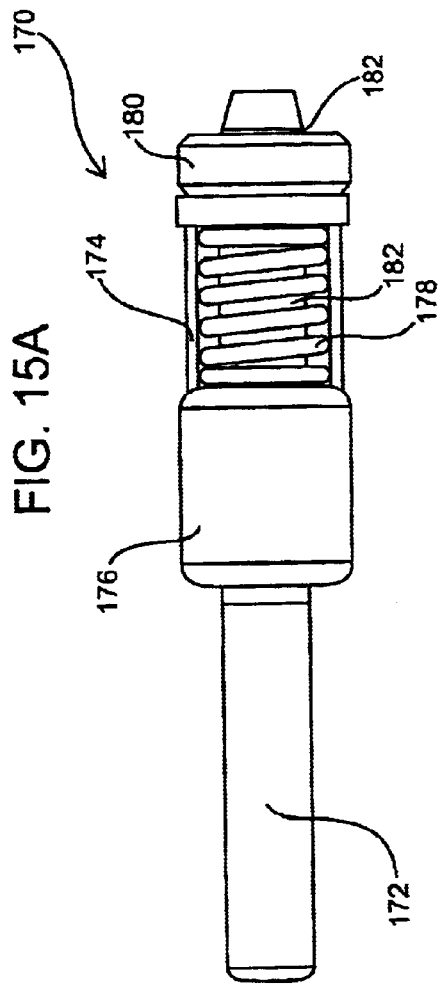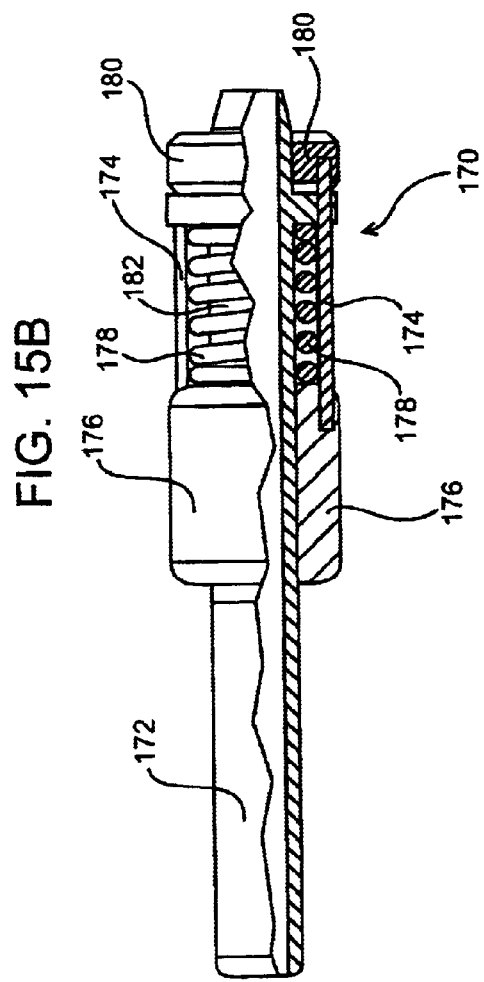

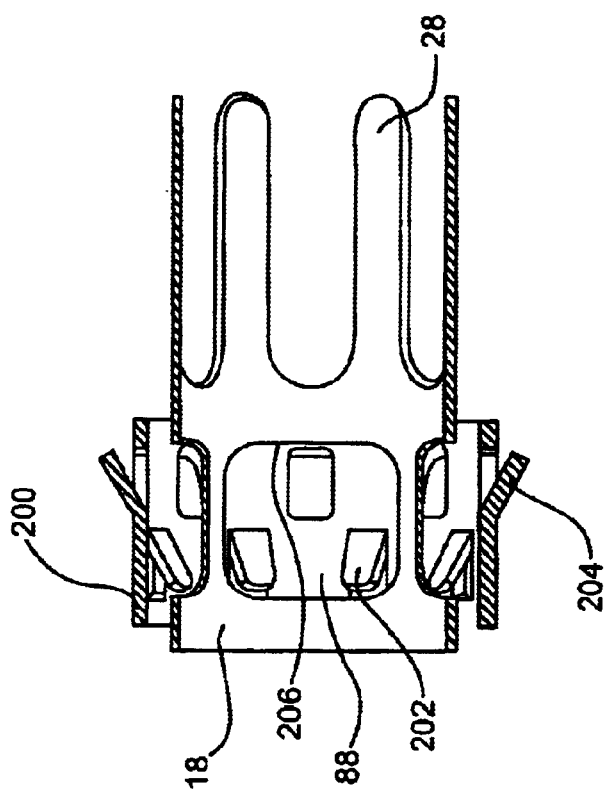
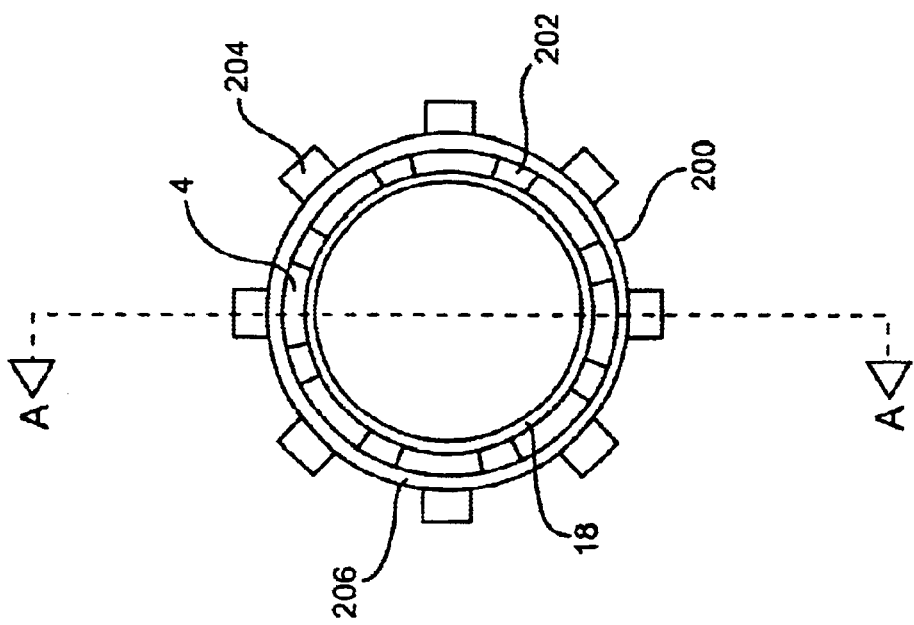
FIG. 16B
FIG. 16C

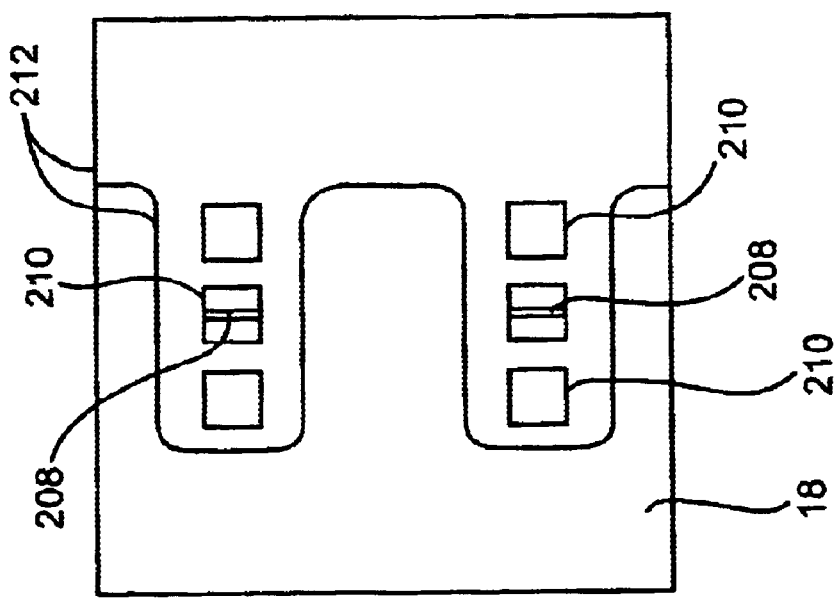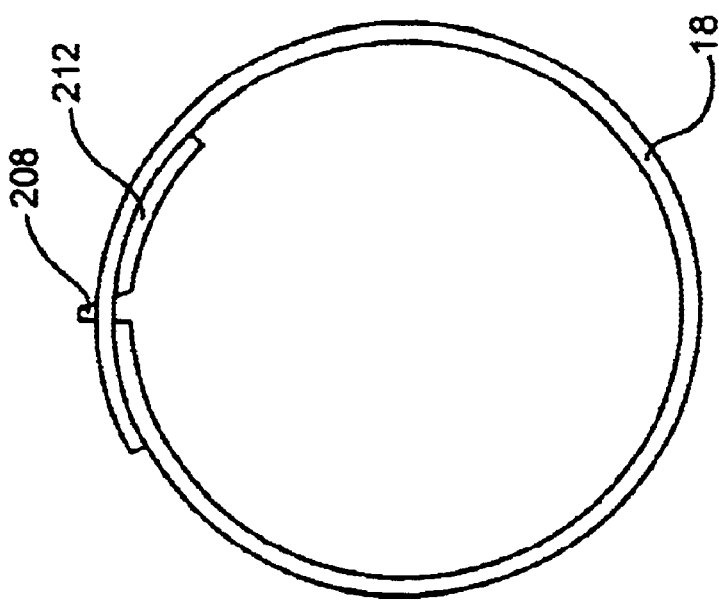

ANASTOMOSIS SYSTEM

CROSS-REFERENCE TO RELATED APPLICATIONS

This application claims the benefit of priority to U.S. Provisional Patent Application Serial No. 60/178,822, entitled "Advanced Anastomosis Systems", filed Jan. 28, 2000, and is related to U.S. Provisional Patent Application Serial No. 60/169,104, entitled "Improved Anastomosis Systems", filed Dec. 6, 1999; U.S. Provisional Patent Application Serial No. 60/151,863, entitled "Additional Sutureless Anastomosis Embodiments", filed Sep. 1, 1999; and co-pending U.S. patent application Ser. No. 09/329,503, entitled "Sutureless Anastomosis Systems", filed Jun. 10, 1999, each of which is incorporated herein by reference in its entirety.

FIELD OF THE INVENTION

This invention relates to devices for deploying and securing the ends of bypass grafts designed to provide a fluid flow passage between at least two host vessel regions (or other tubular structure regions). More particularly, the invention relates to bypass grafts that are secured at target host vessel locations thereby producing a fluid flow passage from the first host vessel location through the bypass graft and to the second host vessel location. The bypass grafts and deployment systems of the invention do not require stopping or re-routing blood flow to perform an anastomosis between a bypass graft and a host vessel. Accordingly, this invention describes sutureless anastomosis systems that do not require cardiopulmonary bypass support when treating coronary artery disease.

Current techniques for producing anastomoses during coronary artery bypass grafting procedures involve placing the patient on cardiopulmonary bypass support, arresting the heart, and interrupting blood flow to suture, clip, or staple a bypass graft to the coronary artery and aorta; cardiopulmonary bypass support is associated with substantial morbidity and mortality. The embodiments of the invention position and secure bypass grafts at host vessel locations without having to stop or re-route blood flow. Accordingly, the embodiments of the invention do not require cardiopulmonary bypass support and arresting the heart while producing anastomoses to the coronary arteries. In addition, the embodiments of the invention mitigate risks associated with suturing, clipping, or stapling the bypass graft to the host vessel(s); namely, bleeding at the attachment sites and collapsing of the vessel around the incision point.

The invention addresses vascular bypass graft treatment regimens requiring end-side anastomoses to attach bypass grafts to host vessels. The scope of the invention includes improvements to the systems used to position and secure bypass grafts for treating vascular diseases such as atherosclerosis, arteriosclerosis, fistulas, aneurysms, occlusions, and thromboses. The improvements to the bypass grafts and delivery systems of the invention also aid in attaching the ends of ligated vessels, replacing vessels harvested for bypass grafting procedures (e.g., radial artery), and reestablishing blood flow to branching vessels which would otherwise be occluded during surgical grafting procedures (e.g., the renal arteries during abdominal aortic aneurysm treatment). In addition, the invention addresses other applications such as, but not limited to, producing arterial to venous shunts for hemodialysis patients, bypassing lesions and scar tissue located in the fallopian tubes causing infertility, attaching the ureter to the kidneys during transplants, and treating gastrointestinal defects (e.g., occlusions, ulcers, obstructions, etc.).

BACKGROUND OF THE INVENTION

Stenosed blood vessels can cause ischemia, which may lead to tissue infarction. Conventional techniques to treat partially or completely occluded vessels include balloon angioplasty, stent deployment, atherectomy, and bypass grafting.

Coronary artery bypass grafting (CABG) procedures to treat coronary artery disease have traditionally been performed through a thoracotomy with the patient placed on cardiopulmonary bypass support and using cardioplegia to induce cardiac arrest. Cardiac protection is required when performing bypass grafting procedures associated with prolonged ischemia times. Current bypass grafting procedures involve interrupting blood flow to suture or staple the bypass graft to the host vessel wall and create the anastomoses. When suturing, clipping, or stapling the bypass graft to the host vessel wall, a large incision is made through the host vessel and the bypass graft is sewn to the host vessel wall such that the endothelial layers of the bypass graft and vessel face each other. Bypass graft intima to host vessel intima apposition reduces the incidence of thrombosis associated with biological reactions that result from blood contacting the epithelial layer of a harvested bypass graft. This is especially relevant when using harvested vessels that have a small inner diameter (e.g., $\leq 2$ mm).

Less invasive attempts for positioning bypass grafts at target vessel locations have used small ports to access the anatomy. These approaches use endoscopic visualization and modified surgical instruments (e.g., clamps, scissors, scalpels, etc.) to position and suture the ends of the bypass graft at the host vessel locations. Attempts to eliminate the need for cardiopulmonary bypass support while performing CABG procedures have benefited from devices that stabilize the motion of the heart, retractors that temporarily occlude blood flow through the host vessel, and shunts that re-route the blood flow around the anastomosis site. However, stabilizers and retractors still require significant time and complexity to expose the host vessel and suture the bypass graft to the host vessel wall. Shunts not only add to the complexity and length of the procedure, but they also require a secondary procedure to close the insertion sites proximal and distal to the anastomosis site.

Attempts to automate formation of sutureless anastomoses have culminated into mechanical stapling devices. Mechanical stapling devices have been proposed for creating end—end anastomoses between the open ends of transected vessels. U.S. Pat. Nos. 4,607,637, 4,624,257, 4,917,090, and 4,917,091, all to Berggren et al., describe an automatic stapling device for use in microsurgery. U.S. Pat. No. 4,214,587 to Sakura describes a mechanical end—end stapling device designed to reattach severed vessels. U.S. Pat. No. 5,503,635 to Sauer et al. teaches another mechanical end—end device that inserts mating pieces into each open end of a severed vessel. Once positioned, the mating pieces snap together to bond the vessel ends.

These end—end devices are amenable to reattaching severed vessels but are not suitable to producing end—end anastomoses between a bypass graft and an intact vessel, especially when exposure to the vessel is limited.

Mechanical stapling devices have also been proposed for end-side anastomoses. These devices are designed to insert bypass grafts, attached to the mechanical devices, into the host vessel through a large incision and secure the bypass graft to the host vessel. U.S. Pat. Nos. 4,366,819, 4,368,736, and 5,234,447, all to Kaster, describe vascular stapling apparatus for producing end-side anastomoses.

U.S. Surgical has developed automatic clip appliers that replace suture stitches with clips. These clipping devices have been demonstrated to reduce the time required when producing the anastomosis but still involve making a large incision through the host vessel wall.

Gifford et al. provides end-side stapling devices as described in U.S. Pat. No. 5,695,504. These devices secure harvested vessels to host vessel walls while maintaining intima-to-intima apposition.

U.S. Pat. Nos. 4,657,019, 4,787,386, and 4,917,087 to Walsh et al. teach a similar end-side stapling device having a ring with tissue piercing pins.

These end-side stapling devices require insertion through a large incision, which dictates that blood flow through the host vessel must be interrupted during the process. Even though these and other clipping and stapling end-side anastomotic devices have been designed to decrease the time required to create the anastomosis, interruption of blood flow through the host vessel increases the morbidity and mortality of bypass grafting procedures, especially during beating heart CABG procedures. A recent experimental study of the U.S. Surgical ONE-SHOT anastomotic clip applier observed abrupt ventricular fibrillation during four of fourteen internal thoracic artery to left anterior descending artery anastomoses in part due to coronary occlusion times exceeding 90 seconds (Heijmen et al., "A Novel One-Shot Anastomotic Stapler Prototype for Coronary Bypass Grafting on the Beating Heart: Feasibility in the Pig." *J Thorac Cardiovasc Surg.* 117:117–25; 1999).

A need thus exists for bypass grafts and delivery systems that are capable of quickly producing an anastomosis between a bypass graft and a host vessel wall without having to stop or re-route blood flow. These anastomoses must withstand the pressure exerted by the pumping heart and ensure blood does not leak from the anastomoses into the thoracic cavity, abdominal cavity, or other region exterior to the vessel wall.

SUMMARY OF THE INVENTION

This invention provides improvements to the sutureless anastomosis systems that enable a physician to quickly and accurately secure a bypass graft to a host vessel or other tubular body structure. The delivery processes of the invention do not require stopping or re-routing blood flow while producing the anastomosis; current techniques require interrupting blood flow to suture, clip, or staple a bypass graft to the host vessel wall.

The fittings of the invention are intended to secure biological bypass grafts, obtained by harvesting vessels from the patient or another donor patient, or synthetic bypass graft materials to a patients host vessel. When using harvested vessels, the fitting embodiments should accommodate a variety of harvested vessel sizes and wall thicknesses. When using synthetic bypass graft materials, the fittings may be incorporated in the bypass graft design to eliminate the step of attaching the bypass graft to the fitting prior to deploying the bypass graft and fitting.

One aspect of the invention provides improved fitting embodiments designed to compress into a reduced diameter while attaching the bypass graft to the fitting and/or deploying the fitting through the delivery system. Once deployed, the compressible fittings of the invention expand towards their preformed geometry such that they exert radial force at the vessel attachment sites; this helps maintain the patency of the anastomosis.

Another aspect of the invention provides additional angled fittings designed to produce anastomoses between bypass grafts and host vessels such that the angle between the bypass graft and the host vessel reduces turbulent flow near the anastomosis. The angled fittings may also be designed compressible.

Another aspect of the invention includes improved support devices capable of securing the end-side fitting to the host vessel and provide a smooth transition from the anastomosis site to the body of the bypass graft.

A further aspect of the invention involves deployment sheaths that facilitate removing from around the bypass graft after inserting and securing the end-side fitting. Various deployment sheath embodiments utilize locking mechanisms to maintain pre-split deployment sheaths in a closed orientation. The locking mechanisms facilitate removal with optimal force, which is preferred to current splittable sheaths that require substantial effort to tear the hub, valve, and sheath.

Additional sheathless anastomosis embodiments are disclosed which are designed to insert the petals or securing end of the end-side fitting into the host vessel without having to insert the fitting through a deployment sheath. Additional end-side fitting embodiments that are able to screw or rotate through a small opening in the host vessel wall with or without the use of a guidewire are discussed. Other end-side fitting embodiments that are able to advance through a small opening in the host vessel wall with the use of a guidewire or dilator without having to rotate the end-side fitting are also discussed.

Further features and advantages of the inventions will be elaborated in the detailed description and accompanying drawings.

BRIEF DESCRIPTION OF DRAWINGS

FIG. 1A shows a side view of a dilating end-side fitting of the present invention.

FIG. 1B shows a top view of the dilating end-side fitting of FIG. 1A.

FIG. 1C shows a cross-sectional view of the dilating end-side fitting of FIG. 1A taken along the line A—A.

FIG. 1D shows a top view of a dilating end-side fitting of the present invention in response to an external force (C).

FIG. 1E shows a cross-sectional view of the dilating end-side fitting of FIG. 1D taken along the line B—B.

FIG. 2A shows a bottom view of a dilating end-side fitting of the present invention in a flattened configuration.

FIG. 2B shows a bottom view of a dilating end-side fitting of the present invention configured for host vessels having a relatively large diameter compared with the diameter of the bypass graft.

FIG. 2C shows a top view of a dilating end-side fitting of the present invention configured for host vessels having a relatively medium or small diameter of the present invention.

FIG. 2D shows a bottom view of the dilating end-side fitting of FIG. 2B or 2C configured for introduction through an opening into a host vessel.

FIG. 3A shows a side view of an introducer of the present invention configured to advance the petals of a dilating end-side fitting through an opening into a host vessel.

FIG. 3B shows a bottom view of the introducer of FIG. 3A.

FIG. 3C shows a top view of the introducer of FIG. 3A.

FIG. 3D shows a bottom view of the introducer of FIG. 3A with the petals of a dilating end-side fitting positioned within the introducer.

FIG. 3E shows a side view of the introducer of FIG. 3A with the petals of a dilating end-side fitting positioned within the introducer.

FIGS. 4A and 4B show a bottom view and a top view of the front piece of a two piece dilating end-side fitting of the present invention.

FIGS. 4C and 4D show a side view and a top view of the rear piece of a two piece dilating end-side fitting of the present invention.

FIGS. 5A to 5C show a side view, a top view, and a bottom view of a cutting hockey stick of the present invention for creating incisions along a host vessel.

FIGS. 7A and 7B show a punching dilator of the present invention.

FIGS. 9A and 9B show a side view and a top view of a splittable deployment sheath of the present invention having a remote splitting mechanism.

FIG. 11A shows the insertion of an end-side fitting of the present invention containing an integrated support device to function as a grommet.

FIG. 11B shows a deployed end-side fitting of the present invention containing an integrated support device functioning as a grommet.

FIG. 12 shows a loading tool of the present invention for inserting an end-side fitting and bypass graft combination into a loading sheath.

FIGS. 13A and 13B show a suction plug of the present invention for defining a cavity in which to deploy and secure the end-side fittings.

FIGS. 15A and 15B show a side view, and an exploded side view of a ring-positioning tool of the present invention.

FIGS. 16A to 16C show a perspective view, a top view, and a side-sectional view of a retaining ring of the present invention used to secure a bypass graft to the base of an end-side fitting.

FIGS. 17A and 17B show an end view and a side view of a split base or stem of an end-side fitting of the present invention that incorporates a locking mechanism.

DETAILED DESCRIPTION OF THE INVENTION

Figure 6B:
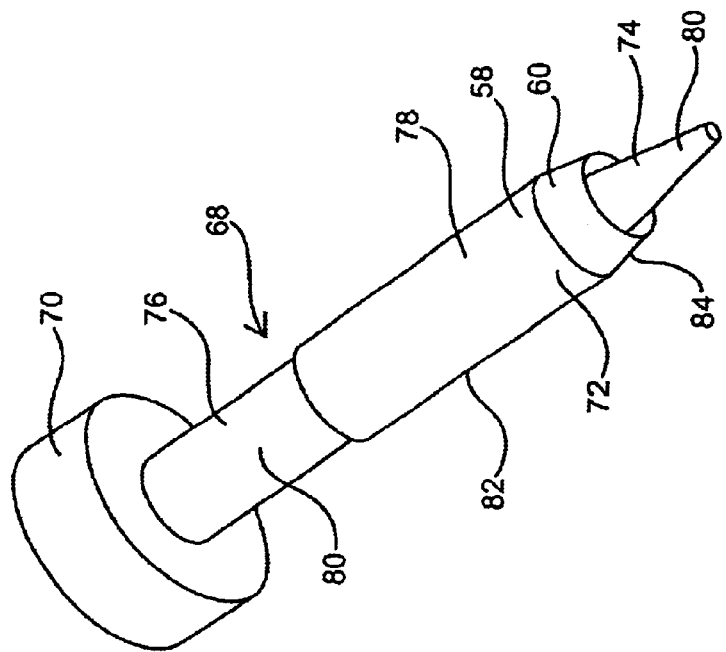
FIGS. 6A and 6B show a cutting dilator of the present invention.

The systems of the invention are intended to produce anastomoses between bypass grafts and host vessels to treat vascular abnormalities such as stenoses, thromboses, other occlusions, aneurysms, fistulas, or other indications requiring a bypass graft. The systems of the invention are also useful in bypassing stented vessels that have restenosed, and saphenous vein bypass grafts that have thrombosed or stenosed.

Current approaches for treating stenosed stents have not been successful at safely and reliably removing the occlusion and opening the vessel lumen. Therefore, the approaches described by this invention, which produce a blood flow conduit around the stented lesion, have the potential to mitigate concerns associated with damaging the stent or forming emboli while removing deposits attached to the stent. The same argument holds true for saphenous vein grafts that have restenosed or thrombosed.

The embodiments of the invention also provide mechanisms to secure branching vessels to a replacement graft during surgical procedures in which the branching vessels would otherwise be occluded from blood flow (e.g., reattaching the renal arteries, mesenteric artery, celiac artery, and intercostal arteries during treatment of abdominal aortic aneurysms that are pararenal, suprarenal, or thoracoabdominal in classification). The embodiments of the invention also enable reattaching the left main artery and right coronary artery during aortic root replacement procedures.

The fitting and delivery system embodiments discussed herein are directly amenable to robotic surgery and less invasive (i.e. minimally invasive) surgery involving a thoracostomy or mini median sternotomy to access the anastomosis site. In particular, the fittings and delivery system embodiments of the invention enable automating the attachment of the bypass graft to the fitting, especially when considering the use of the loading sheath and/or end-side fittings capable of being advanced over a guidewire, as described below. In addition, the deployment and securing systems of the invention are significantly easier to automate than conventional suturing.

Bypass Grafts

The bypass graft may be a synthetic graft material, harvested vessel, or other tubular body structure, depending on the indication for use. The harvested vessels may be an internal mammary artery, mesenteric artery, radial artery, saphenous vein or other body tubing. Harvested vessels may be dissected using newer minimally invasive, catheter-based techniques or standard surgical approaches. The end-side fittings in accordance with the invention are designed to attach bypass grafts to host vessels (or other tubular structures). The fittings used to position and attach such bypass grafts are extensions of the collet and grommet embodiments described in U.S. Pat. No. 5,989,276 to Houser et al., the entirety of which is incorporated herein by reference, and the fittings described in U.S. patent application Ser. No. 09/329,503. The primary advantage of biological bypass grafts (e.g., harvested vessels) over currently available synthetic materials is the reduction in thrombosis especially when using small diameter (e.g., ≦2 mm) bypass grafts. However, the fittings and delivery systems of the invention are equally effective at positioning and securing all types of bypass grafts, biological and synthetic.

Synthetic bypass grafts may be manufactured by extruding, injection molding, weaving, braiding, or dipping polymers such as PTFE, expanded PTFE, urethane, polyamide, polyimide, nylon, silicone, polyethylene, collagen, polyester, PET, composites of these representative materials, or other suitable graft material. These materials may be fabricated into a sheet or tubing using one or a combination of the manufacturing processes stated herein.

The sides of sheet materials may be bonded using radiofrequency energy, laser welding, ultrasonic welding, thermal bonding, sewing, adhesives, or a combination of these processes to form tubing. The synthetic bypass graft may be coated, deposited, or impregnated with materials such as paralyne, heparin solutions, hydrophilic solutions, thromboresistance substances (e.g., glycoprotein IIb/IIIa inhibitors), antiproliferative substances (e.g., Rapamycin), or other substances designed to reduce thrombosis or mitigate other risks that potentially decrease the patency of synthetic bypass grafts. In addition, synthetic bypass grafts may be seeded with endothelial cells, or other biocompatible materials that further make the inner surface of the bypass graft biologically inert.

The primary advantage of synthetic bypass graft materials is the ability to bond the bypass graft to the fittings prior to starting the procedure or incorporate the fittings into the bypass graft by injection molding, adhesive bonding, or other manufacturing process. Currently, synthetic bypass grafts are indicated for blood vessels having medium and large diameters (e.g., >3 mm), such as peripheral vessels, tubular structures such as the fallopian tubes, or shunts for hemodialysis. However, medical device manufacturers such as Thoratec Laboratories, Inc. are evaluating synthetic bypass grafts for coronary indications. In this disclosure and the accompanying drawings, references to bypass graft may pertain to either biological bypass grafts such as harvested vessels or synthetic bypass grafts, unless specifically stated.

As discussed in co-pending U.S. patent application Ser. No. 08/932,566, entitled "Radially Expanding Prostheses and Systems for Their Deployment", filed Sep. 19, 1997, the entirety of which is incorporated herein by reference, and in U.S. Pat. No. 5,989,276, support members may be incorporated into the graft. When using synthetic grafts, the support members may be laminated between layers of graft material. The synthetic graft encompassing support members may be fabricated by extruding, spraying, injection molding, or dipping a primary layer of graft material over a removable mandrel; positioning, winding or braiding the support members on the primary layer; and extruding, spraying, injection molding, or dipping a secondary layer over the graft material/support member combination. The support members may be fabricated from a metal, alloy (e.g., stainless steel or nickel titanium), or polymer (e.g., nylon or polyester); however, the support members preferably have a shape memory. Support members enhance the performance of the bypass graft by maintaining lumenal patency, offering flexibility, and increasing the graft strength. Support members fabricated from memory elastic alloys, such as nickel titanium that exhibit stress-induced martensitic characteristics further reinforce the bypass graft and/or vessel wall and prevent permanent deformation upon exposure to external forces. Such support members also permit compressing the bypass graft into a low profile during deployment through the host vessel wall; the support members urge the bypass graft to expand towards its preformed configuration after the external force (e.g., delivery system) is removed.

End-Side Fittings

The fittings of the present invention consist of one or more components designed to secure a bypass graft to the fitting and the fitting to the host vessel wall to produce a fluid tight bond between the bypass graft and the host vessel. The fittings may be used to produce end-side anastomoses for medium and small diameter vessels (e.g., upper and lower extremity vessels, and coronary vessels) where retrograde blood flow is essential, and end-side anastomoses for large diameter vessels (e.g., the aorta, the iliac artery). The fittings and delivery systems described below may be modified to accommodate end—end anastomoses by reducing, reshaping, or eliminating the petals from the design.

The end-side fittings are constructed from a metal (e.g., titanium), alloy (e.g., stainless steel or nickel titanium), thermoplastic (e.g., PTFE), thermoset plastic (e.g., polyethylene terephthalate, or polyester), silicone or combination of the aforementioned materials into a composite structure; other materials may alternatively be used. For example, end-side fittings fabricated from nickel titanium may be clad with expanded PTFE, polyester, PET, or other material that may have a woven or porous surface. The fittings may be coated with materials such as paralyne or other hydrophilic substrates that are biologically inert and reduce the surface friction. To further reduce the surface tension, metallic or metallic alloy fittings may be electropolished. Evidence suggests that electropolishing reduces platelet adhesion because of the smooth surface. Alternatively, the fittings may be coated with heparin, thromboresistance substances (e.g., glycoprotein IIb/IIIa inhibitors), antiproliferative substances (e.g., Rapamycin), or other coatings designed to prevent thrombosis, hyperplasia, or platelet aggregation around the attachment point between the bypass graft and the host vessel. Alternatively, materials such as platinum, gold, tantalum, tin, tin-indium, zirconium, zirconium alloy, zirconium oxide, zirconium nitrate, phosphatidyl-choline, pyrolytic carbon, alloys or combinations of these, or other materials, may be deposited onto the fitting surface using electroplating, sputtering vacuum evaporation, ion assisted beam deposition, vapor deposition, silver doping, boronation techniques, a salt bath, or other coating process. A still further improvement of the fittings is to include beta or gamma radiation sources on the end-side fittings. A beta or gamma source isotope having an average half-life of approximately 15 days such as phosphorous 32 or palladium 103 may be placed on the base and/or petals of the end-side fitting using an ion-implantation process, chemical adhesion process, or other suitable method.

End-side fitting embodiments may be fabricated from a tube of material having a desired cross-sectional geometry. The desired pattern of petals, tabs, holes, slots, and spaces may be fabricated on the tubular metal material and may be formed using chemical etching, electron discharge machining (EDM), laser cutting, or other manufacturing process. These end-side fittings may be maintained as a complete tube or may be fabricated to incorporate a gap between opposite sides to make the fitting compressible and expandable, as will be discussed below.

Alternatively, the end-side fitting embodiments may be fabricated from a sheet of material cut into the desired pattern and formed (e.g., through an annealing process) into the desired cross-sectional geometry (circular, elliptical, or other shape), as shown in FIGS. 2A to C. The sides of the fitting may be bonded to form an enclosed tube or may be formed with a gap between opposite sides to enable compressing the fitting into a reduced diameter for positioning the bypass graft over the base of the fitting and inserting the fitting through an opening into a host vessel having a diameter less than the expanded diameter of the fitting. Such compressible fittings also facilitate sizing issues since they accommodate a wide range of bypass graft sizes.

To produce these end-side fittings, the raw material may be fabricated into the desired pattern by chemically etching, EDM, laser cutting, or other manufacturing process. End-side fittings fabricated from sheet stock are then wrapped around mandrels having the desired resting cross-sectional profile(s) and the end-side fitting is heated until it assumes this configuration. If the sides are to be bonded, spot welding, laser welding, or other manufacturing process may be employed.

When forming the resting configuration of the compressible and expandable split-wall end-side fitting, a gap is produced between opposite sides of the base or stem 18 of the fitting. The gap between the sides of the fitting permits compressing the end-side fitting into a reduced diameter which facilitates positioning the bypass graft over the base of the fitting and/or advancing the fitting through a delivery system having an inner diameter less than the outer diameter of the fitting in its expanded, resting configuration. This split-wall end-side fitting is also expandable so it may be enlarged for advancing outside a bypass graft everted over or positioned over a central member. In this case, the split-wall end-side fitting secures the bypass graft against the central member. In addition, this enables using a single fitting configuration to accommodate a wide range of bypass graft sizes.

FIGS. 17A and 17B show the base 18 of a split-wall end-side fitting that incorporates a latching mechanism to lock opposing sides of the fitting base or stem 18 together. On one side of the base or stem 18, extensions 208 function as teeth and are formed in the base or secured using welding or other bonding process. The extensions or teeth 208 are biased, as shown in FIG. 17A, to readily advance one way and prevent movement in the opposite direction when positioned within spaces 210 created on the opposite side of the base or stem 18. This enables locking the base or stem at a smaller diameter around a bypass graft positioned over a central member to compress the bypass graft against the central member. If the teeth are biased in the opposite direction (not shown), the base or stem 18 may be locked at an enlarged diameter to produce a compression fit against the bypass graft positioned outside the stem or base and a retaining ring used to secure the bypass graft to the fitting base or stem 18. When opposite sides of the base or stem 18 are locked together, an overlap 212 is produced providing a blood impervious barrier between opposing sides of the split base or stem 18.

The base of the fitting (as well as the petals if desired) may be covered with a blood impervious, porous, compliant material such as silicone, urethane, expanded PTFE, PTFE, FEP, polyester, PET, or other material. The covering over the base of the fitting may be fabricated with dipping, injection molding, cladding, or other manufacturing process. This covering enables compressing and expanding the base and/or petals of the fitting yet maintains the leak resistance of the anastomosis and isolates the cut end of the bypass graft from blood.

Figure 8:
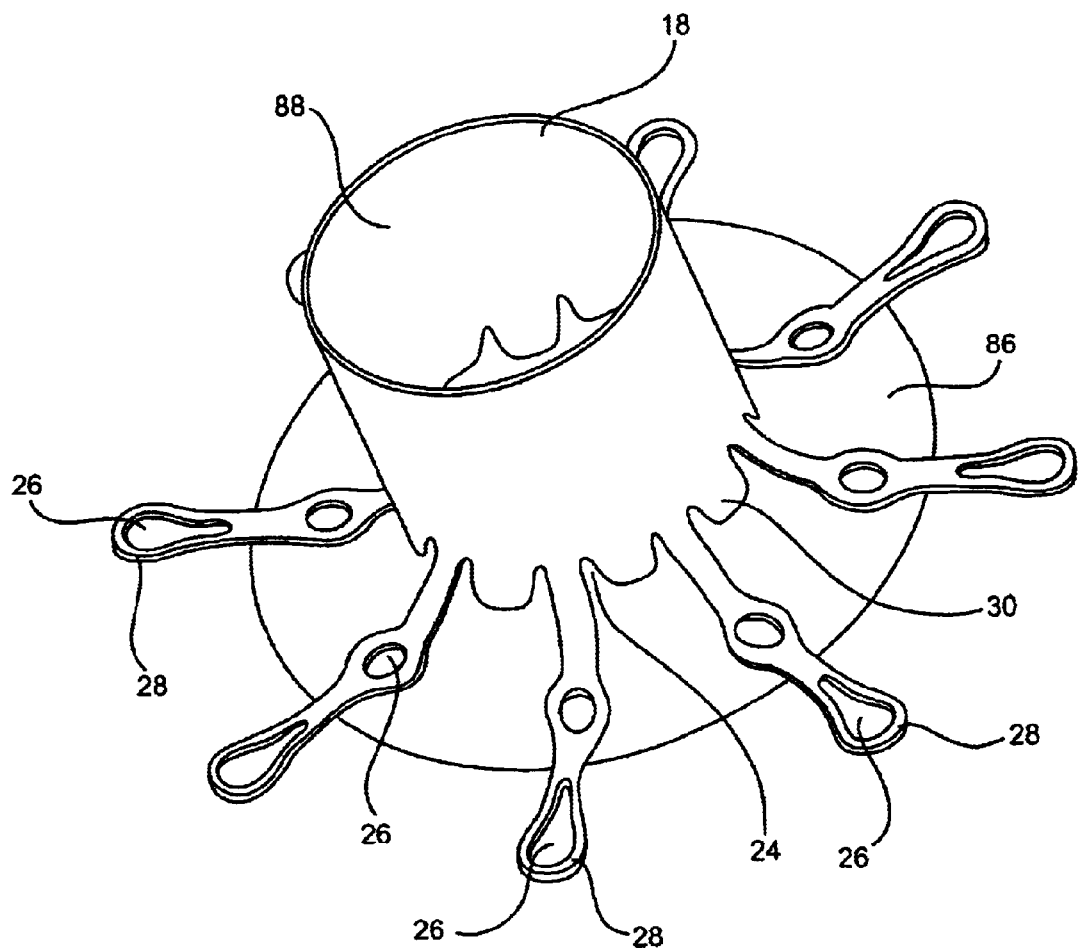
FIG. 8 shows an end-side fitting of the present invention having a covering to enhance hemostasis of the anastomosis.

As shown in FIG. 8, the covering 86 may be configured as a separate component, which may or may not be attached to the end-side fitting. In this case, the covering isolates holes, spaces, and slots created in the end-side fitting which may otherwise provide a potential pathway for blood leakage. The covering 86 may be secured to the base or stem of the fitting 18 by inserting sutures through the proximal end of the covering and holes 88 in the base; the sutures would then be tied to attach the proximal end of the covering to the fitting base. In a similar manner the covering 86 may be attached to the petals 28 of the fitting at holes 26 fabricated at desired locations along the petals.

Alternatively, the covering 86 may be bonded to the stem or base of the fitting, and/or petals by mechanical compression through the use of shrink tubing (e.g., PET, FEP, polyester, etc.). For example, the proximal end of the covering 86 may be positioned over the base or stem of the fitting and a piece of shrink tubing is positioned over the covering to base interface. Once positioned, the shrink tubing is heated or otherwise allowed to decrease in diameter thereby compressing the proximal end of the covering against the base of the fitting. To enhance this bond adhesives may be applied to the edge(s) of the shrink tubing. Such suitable bonding agents include cyanoacrylate, UV-curable adhesive, epoxy, or other adhesives.

The covering 86 may be adhesively bonded to the end-side fitting at the base and/or petals. An adhesive bond between the covering 86 and the fitting petals and/or base may be enhanced by a number of treatment processes including 1) applying an adhesive primer to the fitting surfaces; 2) modifying the bonding surface of the covering 86 utilizing corona discharge, plasma etching, chemical etching, or other surface modification techniques.

Alternatively, the covering may be laminated, cladded, or sintered around the petals and/or base by placing matched layers on the inside surface and outside surface of the fitting and thermally bonding the layers producing a secure bond between the covering and the end-side fitting. Holes or slots in the petals may and/or stem may also aid in cladding or laminating by providing contact areas for producing bonds between materials placed on each side of the holes.

The distal section of the covering 86 does not necessarily need to be secured to the petals but may incorporate slits into or through which the petals may be inserted. This enables movement of the petals relative to the covering. Still, another option is to incorporate the covering at the distal end of a synthetic bypass graft and securing the bypass graft using previously discussed methods. The covering end of this modified bypass graft may be secured to the petals of the fitting such that the petals do or do not move relative to the covering. Alternatively, the covering end of the bypass graft may not be secured to the petals since the engagement of the petals against the interior surface of the host vessel in turn positions the covering end of the bypass graft between the petals and the interior surface of the host vessel.

Alternatively, the covering 86 may be fabricated from a combination of at least two different materials having specific purposes. For example, the proximal end, adapted to engage the base or stem of the end-side fitting and isolate spaces, holes, or slots in the base or stem, may be fabricated from an elastic, blood impervious material, and the distal end of the covering may be relative inelastic and incorporate a textured surface (e.g., woven Dacron or woven PTFE) to maintain the porosity necessary for endothelialization or other purposes. The different materials may be thermally bonded together or secured with adhesives or other methods.

When incorporating a covering layer on the interior surface of the base or stem of the fitting, the bond between the outer end-side fitting and an everted or non-everted bypass graft positioned inside the base and secured to a central fitting member (not shown) is improved. The inside covering layer provides a more atraumatic, blood impervious seal between the interior surface of the fitting base or stem and the external surface of the bypass graft. The covering layer is fabricated on the interior surface of the base or stem of the fitting using the same manufacturing processes as described above for positioning and securing a covering layer on the external surface of the fitting base or stem.

The petals in many of these fitting embodiments are shown straight (i.e. at an angle of approximately zero degrees from the base of the fitting). During manufacture, the petals may be thermally formed at any angle between about 30 degrees and about 150 degrees from the base of the fitting such that the petals contact the interior surface of the host vessel once the fitting is inserted through the host vessel wall. The petals, having an angle between about 30 degrees and about 150 degrees from the base of the fitting in their resting orientation, also compress into a reduced outer diameter during deployment through delivery system and expand towards their resting configuration once deployed inside the host vessel. The number of petals incorporated in the end-side fitting design depends on the size of the bypass graft and the size of the host vessel. The number of petals also depends on the desired tensile strength between the fitting and the host vessel; increasing the number of petals in turn increases the force required to pull the fitting petals out of the host vessel. After advancing the fitting through an opening into the host vessel wall, the bypass graft and fitting combination is gently retracted to engage the interior vessel wall with the petals. For mechanical securing, a support device is advanced over and locked to the fitting thereby compressing the vessel wall against the petals.

Figure 16A:
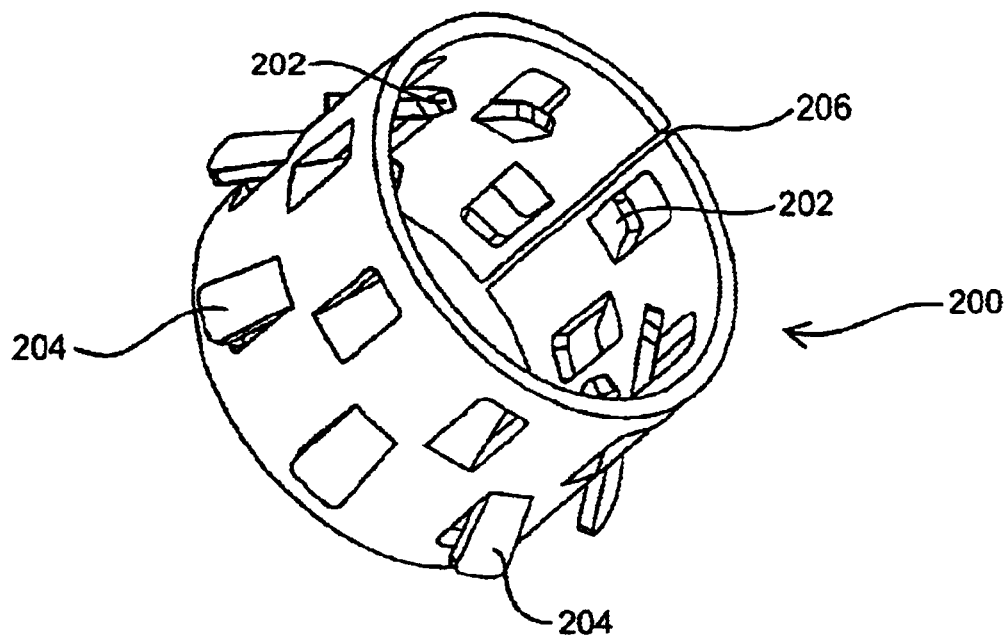

As previously discussed in co-pending U.S. Provisional Patent Application Serial No. 60/151,863 and co-pending U.S. patent application Ser. No. 09/329,503, the bypass graft may be secured to the base or stem 18 of an end-side fitting by advancing the bypass graft over the outside surface of the base or stem and positioning a retaining ring or clip. FIGS. 16A to 16C show an improvement to the retaining rings or clips previously described. The retaining clip 200 incorporates inner tabs 202 and outer tabs 204, and a gap 206 between opposing sides. The gap 206 permits expansion of the retaining ring or clip into an enlarged diameter for positioning over the bypass graft 4 and fitting base interface, as shown in FIG. 16C. Once positioned, the external force causing the retaining clip to enlarge is removed enabling the retaining clip to return towards its resting, smaller diameter configuration. The inner tabs 202 are oriented such that when the inner tabs 202 are positioned within matching spaces 88 of the fitting base or stem 18 (as shown in FIG. 16B) the inner tabs 202 lock the retaining clip to the fitting base or stem 18. The outer tabs 204 provide a locking mechanism to secure the support device, described below, against the host vessel wall to enhance the attachment of the end-side fitting to the host vessel wall.

FIGS. 15A and 15B show a positioning tool used to manipulate any expanded device retaining ring, (previously described), expandable and collapsible end-side fitting (described above), or support device (described below) over another fitting component. The positioning tool incorporates a longitudinal slot so the tool may be removed from the side of the bypass graft after positioning an enlarged retaining ring to secure the bypass graft against the base of the end-side fitting, after positioning an expanded end-side fitting over a bypass graft everted over a central member, or after positioning an expanded support device over the base of the end-side fitting. The expanded fitting component is positioned over the main body tube 182, which incorporates a longitudinal slot to permit removal of the positioning tool from the side of a bypass graft. The expanded fitting component (not shown) is positioned into contact with the distal end of the deployment collar 176. The deployment collar runs along at least two slide pins 174 to advance the expanded fitting component towards the pusher collar 180; the deployment collar and pusher collar also incorporate a longitudinal slot to permit removal from around the side of the bypass graft. Once the expanded fitting component is advanced beyond the distal end of the main body tube 182, it returns towards its reduced diameter, resting configuration. A return spring 178 urges the deployment collar 176 away from the pusher collar 180 to prevent unwanted advancement of the deployment collar 176, which could place the expanded fitting component erroneously. The positioning tool 170 is remotely manipulated using a proximal handle 172.

Support Devices

After positioning the end-side fitting inside the vessel such that the base of the fitting extends through an opening into the host vessel wall and the petals contact the interior surface of the host vessel, the support device is positioned over the base of the fitting and locked in place. The end-side fittings may incorporate tabs, threads, or other locking mechanism with which to secure a support device to the end-side fitting. The support device is alternatively locked to the base of the fitting using adhesives, implantable clips, staples, sutures, or other attachment means.

The support device may be constructed from polyethylene, polyurethane, polycarbonate, PEEK, silicone, nickel titanium, spring stainless steel, other alloy, combination of the aforementioned materials, or other material that may be extruded, injection molded, rolled, or otherwise formed into a tube having the desired cross-sectional profile. In addition, the support device may incorporate a braided, woven, or wound layer laminated between two polymer layers to resist kinking and improve the column strength and torque response. Alternatively, the support device may be fabricated with a memory elastic central layer encapsulated with a compliant covering. The support device preferably has porosity sufficient to permit air to diffuse into tissue covered by the support device. The pore size may be as high as approximately 100 $\mu$m as long as the porosity is chosen such that blood does not continually leak through the support device. If the pore size is chosen such that it completely restricts blood flow even when the porosity is extremely high then the pore size needs to be less than approximately 8 $\mu$m.

Figure 10A:
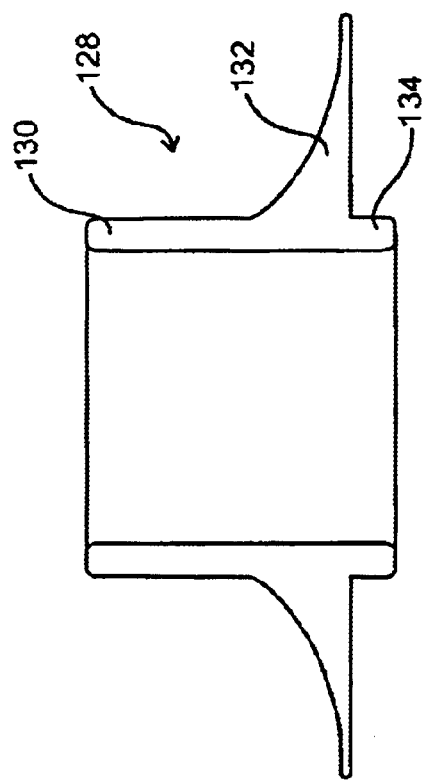
FIGS. 10A and 10B show a side view and a side-sectional view of a support device of the present invention having a protrusion to enhance hemostasis of the anastomosis.
Figure 10B:
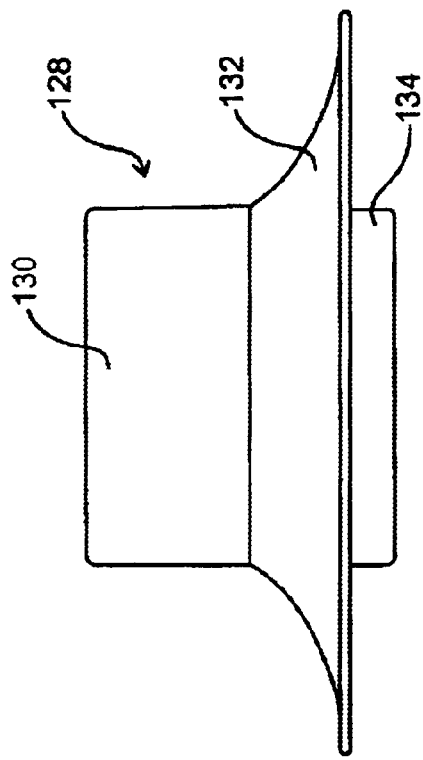

The support device shown in FIGS. 10A and 10B, may include an integrated interface sealer 134 designed to further eliminate blood leakage at the opening between the host vessel wall and the base of the fitting. The interface sealer 134 is positioned at the opening between the base of the fitting and the host vessel wall while positioning the support device 130. The interface sealer 134 may comprise a component attached to (e.g., using adhesives, thermal bonding, ultrasonic welding, or other process) but different from the main section of the support device component and may be fabricated from collagen, fibrin structures, PTFE mesh, or other materials known to promote cellular growth or platelet adhesion and result in sealing or stabilization of the anastomosis site. Alternatively, the interface sealer 134 is fabricated from the same material as the main section of the support device during the injection molding or other manufacturing process used to fabricate the support device. The interface sealer 134 is preferably compliant and capable of deforming to match gaps or voids between the opening through the host vessel wall and the base of the fitting.

For certain end-side fitting embodiments, especially the sheathless embodiments discussed below, the support device may be incorporated on the base or stem of the end-side fitting as an attached component. These embodiments are improvements to the grommet designs described in U.S. Pat. No. 5,989,276. FIGS. 11A and 11B show a side-sectional view of an end-side fitting incorporating a support device 136 attached to the base or stem 18 of the fitting. The base of the end-side fitting may incorporate holes 88 as shown in FIGS. 8 and 11A in which the support device may be laminated, adhesively bonded, or secured using another mechanism. Alternatively, the support device may be fabricated from the same material as the base of the end-side fitting; this is especially relevant when the end-side fitting does not need to have a memory elastic component and may be fabricated by injection molding the fitting. As shown in FIG. 11A, the support device 136 maintains its position while the petals 28 are compressed into a reduced diameter (for those versions that utilize compressible/expandable petals). Once the petals 28 are positioned inside the host vessel, the petals return towards their resting configuration compressing the host vessel wall against the support device 136. The support device 136 may be fabricated from a relatively compliant material to provide an atraumatic seal between the host vessel wall and the petals, and enable the support device 136 to accommodate varying host vessel wall thicknesses. The support device 136 incorporates a textured distal surface 140 to increase the contact surface area between the support device and the host vessel wall, and improve the air permeability through the support device and into the host vessel wall. This textured distal surface may be fabricated by attaching a woven or porous material to the distal surface of the support device or incorporating such a pattern during injection molding or other manufacturing process.

Deployment Systems

Conventional anastomosis techniques require a relatively large incision through the vessel wall and use sutures, commercially available clips, or stapling devices to bond the end of the bypass graft to the edges of the punch created in the vessel wall. In certain cases, the structural integrity of the vessel wall may be weakened causing the vessel to collapse at the anastomosis site, especially when the bypass graft is not appropriately aligned to the host vessel incision. Therefore, the deployment system embodiments of the invention are designed to quickly access the host vessel through a small puncture in the vessel wall. As such, the deployment systems are designed to prevent excess blood loss when accessing the host vessel and deploying the bypass graft and fitting combination, thereby eliminating the need to stop or re-route blood flowing through the host vessel. This approach also improves the leak resistance around the fitting due to elastic compression of the vessel wall around the fitting and automatically aligns the bypass graft to the host vessel wall at the anastomosis site.

For surgical applications, physicians are able to access the anastomosis sites from the exterior surface of the host vessel(s). The deployment system of the surgical approach must permit removal after both ends of the bypass graft are secured and the delivery system resides around the attached bypass graft. The deployment system leverages conventional I.V. access techniques to produce an opening through the host vessel wall. Guidewires have commonly been used to gain access into the host vessel after puncturing the host vessel wall with a needle. In addition, the technique of inserting a sheath into a host vessel by advancing it over a dilating mechanism and a guidewire is commonly used when performing the Seldinger technique during catheterization procedures.

The sheath and dilating mechanism of the deployment system, as previously described in U.S. Pat. No. 5,989,276, co-pending U.S. Provisional Patent Application Serial No. 60/151,863, and co-pending U.S. patent application Ser. No. 09/329,503, may be constructed from polyethylene, polycarbonate, PEEK, other polymer, metal, or metal alloy that may be extruded, injection molded, or swaged into a tube having the desired cross-sectional profile. A taper and radius may be formed in the components of the deployment system by thermally forming the tubing into the desired shape or incorporating such features in the injection molding cast. In addition, the components of the deployment system may incorporate a softer distal tip fabricated by thermally bonding a short section of lower durometer tubing to the sheath or tapering the thickness of the sheath tubing.

To prevent the backflow of blood through deployment sheaths, hemostatic valves may be used. The hemostatic valves prevent blood leakage but permit insertion of a device such as a fitting with an attached bypass graft through the sheath. The hemostatic valve of the delivery system of the invention also incorporates a mechanism to separate along at least one side and remove from around the bypass graft. To accomplish this, the hemostatic valve is attached to the hub of the sheath and includes a mechanism to separate along at least one side. To incorporate a splitting mechanism in the deployment sheath, at least one groove, series of perforations, slot, slit, or combination of these features are incorporated in the sheath tubing and hub member. The at least one groove, series of perforations, slot, slit, or combination of these features may be fabricated while injection molding or otherwise manufacturing the sheath tubing and/or hub, or may be formed in the assembled sheath by laser drilling, milling, or other manufacturing process.

Various configurations of splittable deployment sheaths and associated deployment components are discussed in co-pending U.S. Provisional Patent Application Serial No. 60/151,863, and co-pending U.S. patent application Ser. No. 09/329,503. Improvements to the operation of such deployment systems will be identified below and include mechanisms to facilitate splitting the deployment sheath, relieve the stress around the opening through the host vessel, enable remote separation of the splittable sheath for removal from around the bypass graft and preserve hemostasis during the deployment and securing processes.

Figure 14A:
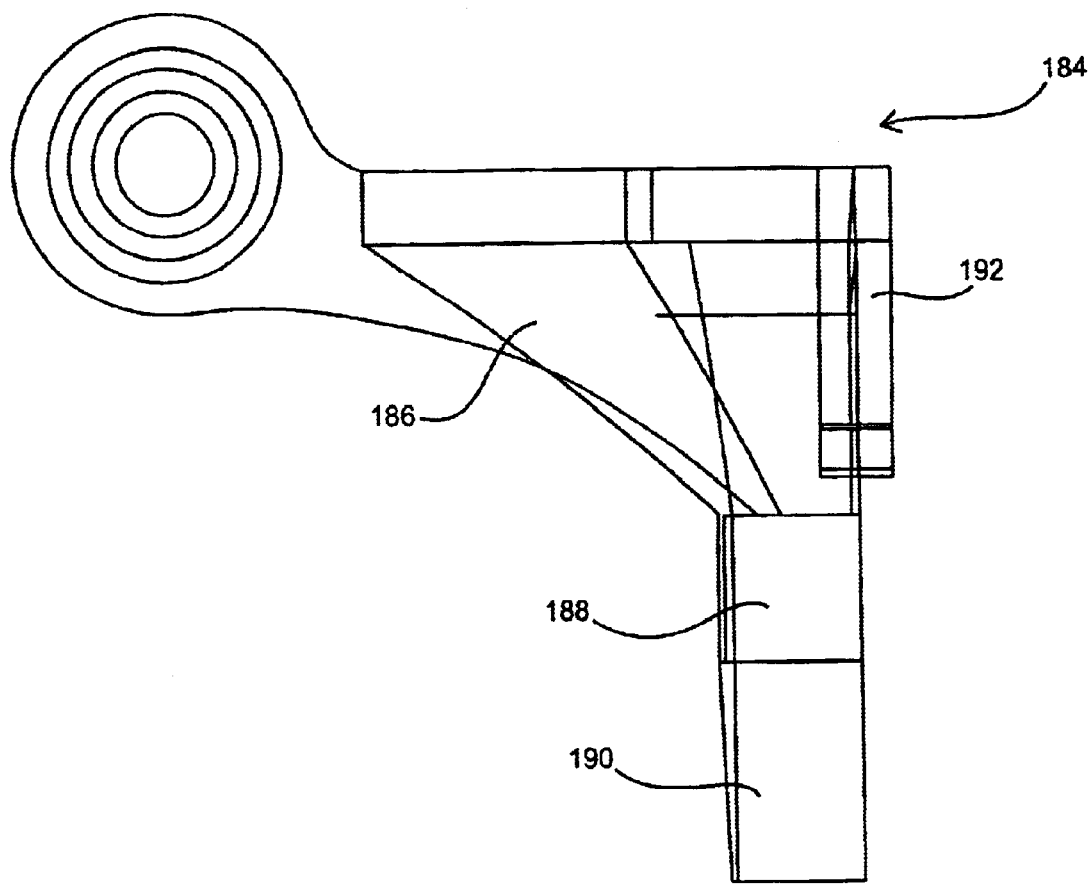
FIGS. 14A to 14C show a side view, an end view, and a perspective view of one half of a pre-split deployment sheath of the present invention.
Figure 14B:
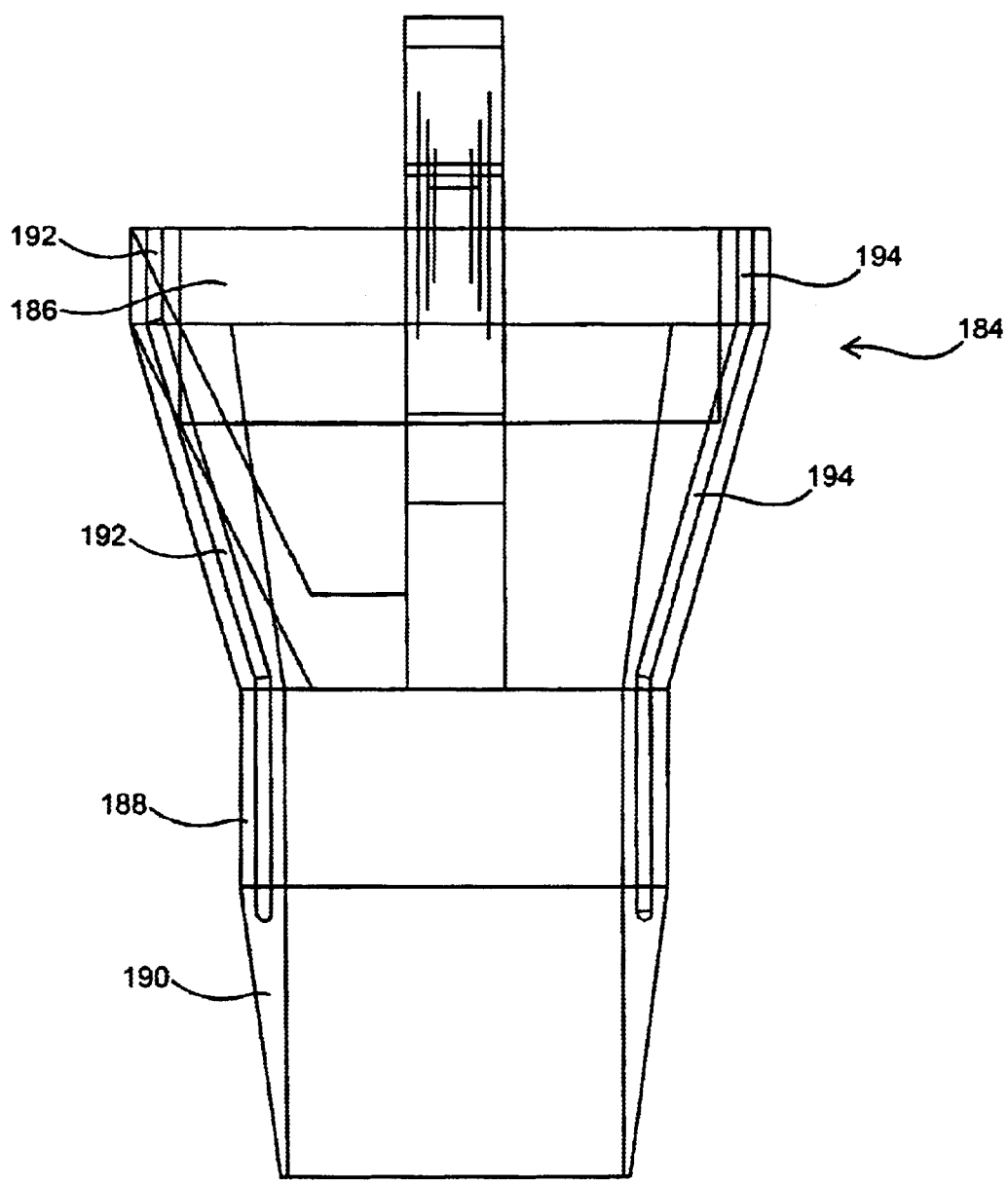
Figure 14C:
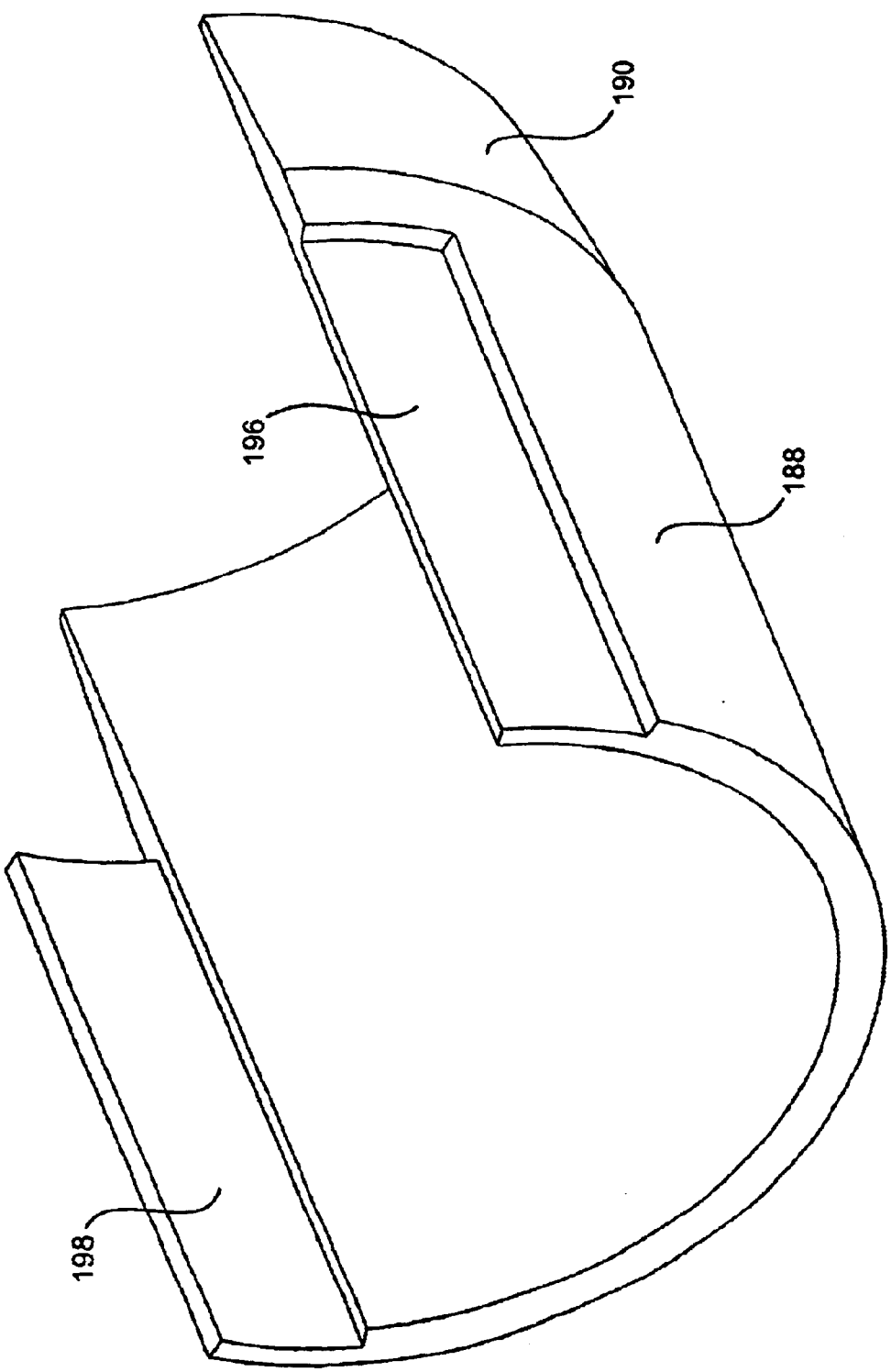

FIGS. 14A to 14C show a modification of the pre-split deployment sheath designed to minimize the wall thickness of the deployment sheath thus the maximum outer diameter to which the opening through the host vessel wall must expand. The deployment sheath, shown in FIGS. 14A and 14B as one half of the deployment sheath, has a latching mechanism that incorporates matching extensions 192 and notches 194 on opposing halves of the deployment sheath. The deployment sheath halves are locked together by inserting the extensions 192 into the notches 194 such that a friction fit occurs between the extensions and notches. This latching mechanism may be augmented by temporary securing devices such as perforated tubing or other mechanism designed to hold the pre-split halves together, yet permit removal so the deployment halves may be separated, as previously described. The extensions and notches are located on the hub 186 of the deployment sheath 184 such that the main body tubing 188 of the deployment sheath does not need to incorporate such a locking mechanism and can have a minimal wall thickness. The deployment sheath also incorporates a distal tapered section 190 to provide a smooth transition from the dilator to the outer diameter of the deployment sheath main body tubing 188. FIG. 14C shows a modification to the main body tubing section 188 of the deployment sheath that provides a locking mechanism to maintain hemostasis through the deployment sheath yet minimizes the wall thickness of the deployment sheath. The main body tubing has matching outer and inner lap joints (198 and 196 respectively) on opposing deployment sheath halves, as shown in FIG. 14C. Engaging opposing deployment sheath halves join the outer and inner lap joints producing a blood impervious seal along the main body tubing 188. The locking mechanism at the hub 186 of the deployment sheath helps maintain the position of the main body tubing lap joints in addition to locking the two deployment sheath halves together, as described above.

Observations during experimental evaluations have demonstrated that over expansion of an opening through a host vessel wall potentially causes radial splitting of the host vessel wall, especially when over expanding small diameter vessels. To prevent this radial splitting, cutting mechanisms like the cutting hockey stick 54 shown in FIGS. 5A to 5C produce short, longitudinal incisions that relieve the stress on a vessel wall produced while dilating the opening. These longitudinal incisions also enable dilating the opening in the host vessel wall to a larger diameter without producing radial splitting than if a cutting mechanism is not utilized. FIGS. 5A to 5C show a cutting hockey stick configured to create longitudinal incisions along the host vessel as guided by a guidewire 6 already inserted into the host vessel (not shown). The cutting hockey stick 54 incorporates a distal lumen 64 to pass over a guidewire 6. A slot 66 permits removal of the cutting hockey stick 54 from around the side of the guidewire 6 without having to feed the lumen of the cutting hockey stick past the free end of the guidewire. The distal end of the cutting hockey stick is atraumatic so as not to cause damage to the opposite vessel wall or the endothelium. A cutting element 58 having a cutting edge 60 is used to create an incision as the hockey stick is advanced over the guidewire. A handle 56 is connected to the main section 62 of the hockey stick and is used to manipulate the cutting hockey stick.

Figure 6A:
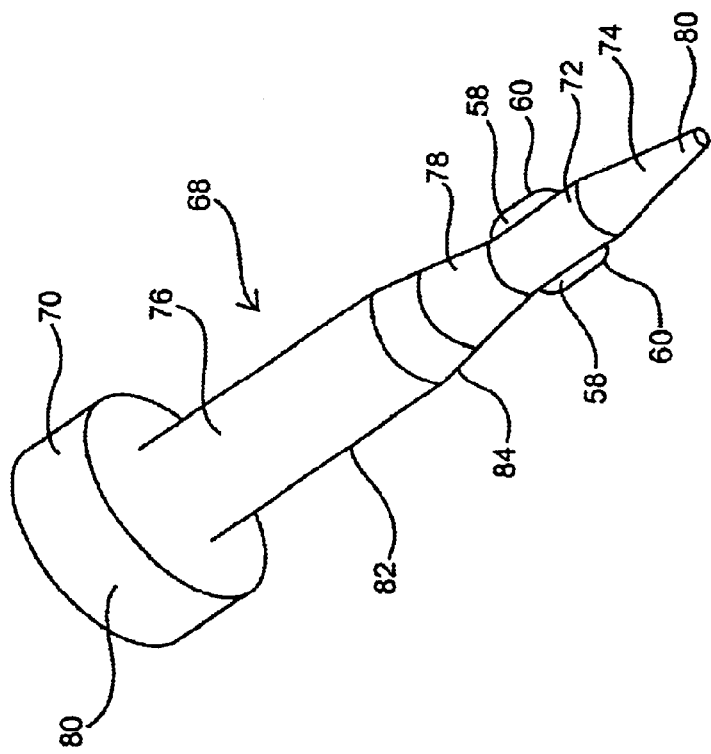

FIGS. 6A and 6B show an alternative cutting mechanism to relieve the stress on the host vessel wall during expansion of the opening. This embodiment is a cutting dilator that incorporates a central lumen 80 so the cutting dilator may pass over a guidewire or needle. The cutting dilator 68 incorporates two sections, a distal section 72 and a proximal section 76. The outer diameter of the distal section is smaller than that for the proximal section to enable expanding the opening through the host vessel wall in steps which provides a better dilation effect as opposed to immediately expanding the opening through the host vessel wall to the large outer diameter. By expanding to a first diameter and leaving the opening at the first diameter for a period of time prior to expanding to the second, larger diameter, the tissue has time to adjust to the first diameter thereby minimizing the potential for splitting, which can occur from a dramatic instantaneous over expansion of the tissue. The distal section 72 has a tapered region 74, which provides a smooth transition from the guidewire or needle to the outer diameter of the distal section. The proximal section 76, in turn, provides a tapered region 78 to provide a smooth transition from the distal section to the outer diameter of the proximal section. The distal section also contains at least one cutting element 58 with at least one cutting edge 60 designed to create at least one incision through the host vessel wall. The embodiment shown in FIGS. 6A and 6B has two cutting elements 58 on opposite sides of the distal section so opposing incisions may be created simultaneously. At least one, and as many as ten, cutting elements may be included in the distal section. In addition, the cutting elements may be staggered along the distal section to produces incisions at the desired locations. The embodiment shown in FIGS. 6A and 6B incorporates a movable tube 82 designed to cover the cutting elements 58 once the dilator is positioned through the opening in the host vessel wall. When the movable tube is positioned in the forward orientation, as shown in FIG. 6B, the cutting elements are covered such that they will not cut or damage tissue in this configuration. This is important so as to prevent endothelial damage after the dilator is positioned and the deployment sheath is being advanced through the opening. A deployment sheath (not shown) may be contained around the cutting dilator and advanced through the opening once the cutting dilator is positioned through the opening.

Figure 6E:
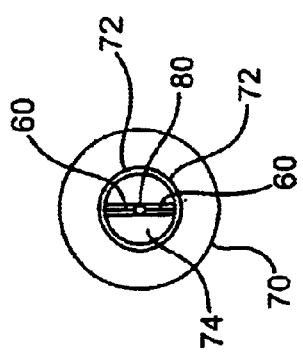
FIGS. 6C to 6E show a side view, bottom view, and top view of a cutting dilator of the present invention.
Figure 6C:
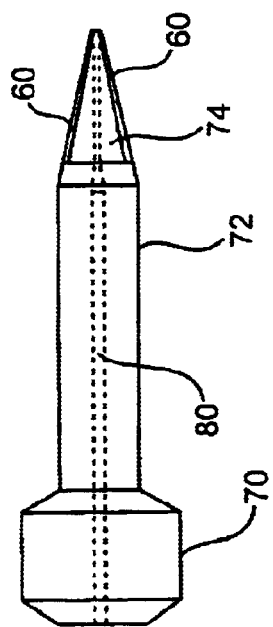
Figure 6D:
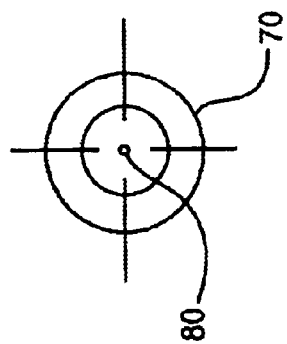

FIGS. 6C to 6E show an alternative cutting dilator that is fabricated from a single piece. As shown in FIG. 6C, the cutting dilator incorporates a tubular distal section 72 having an outer diameter that matches, with suitable tolerance, the inner diameter of the deployment sheath such that the deployment sheath may be advanced through the opening after the cutting dilator has produced and expanded the opening through the host vessel wall. The distal taper 74 is configured to expand the opening and simultaneously create at least one longitudinal incision. A cutting edge 60 is disposed on the distal taper 74 and produces the longitudinal incision(s) to relieve the stress on the host vessel wall and facilitate dilating the opening without causing radial splitting of the host vessel wall. The cutting edge 60 may be fabricated by grinding the distal tapered end 74 into a sharp edge. Alternatively, a sharpened blade may be inserted into notches created in the tapered distal end 74 and secured in place. A proximal handle 70 is attached to the distal section 72 and contains a lumen 80 that is routed through the tubular distal section to the tapered distal end 74 and is configured to pass a guidewire.

Figure 6F:
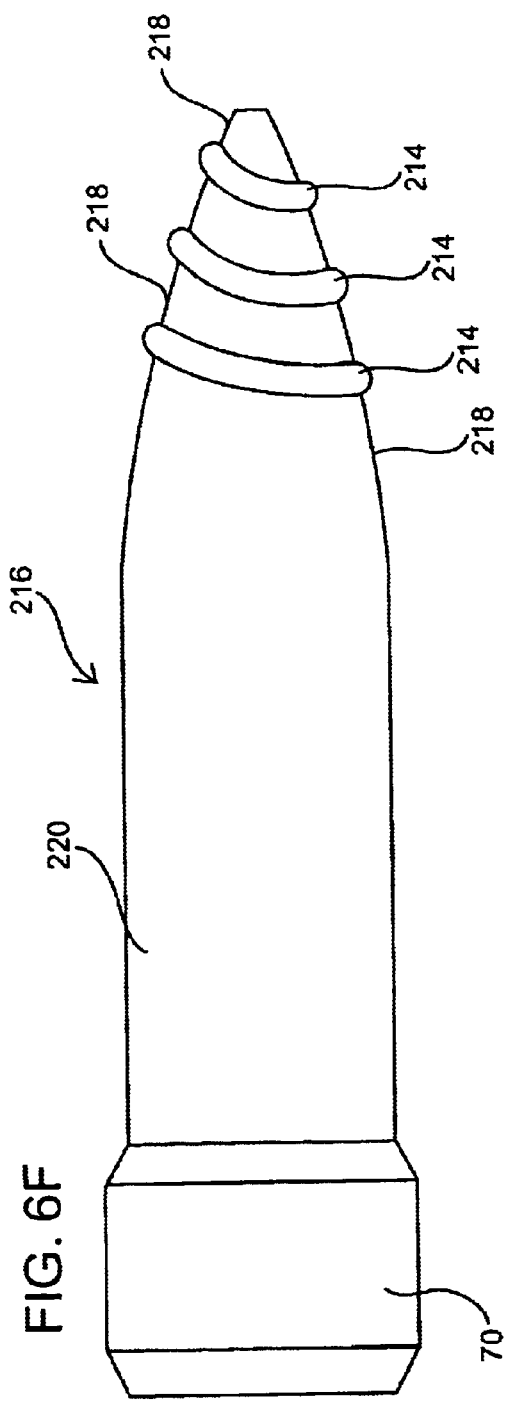
FIGS. 6F and 6G show a side view and a side-sectional view of a screw-in or rotatable dilator of the present invention.
Figure 6G:
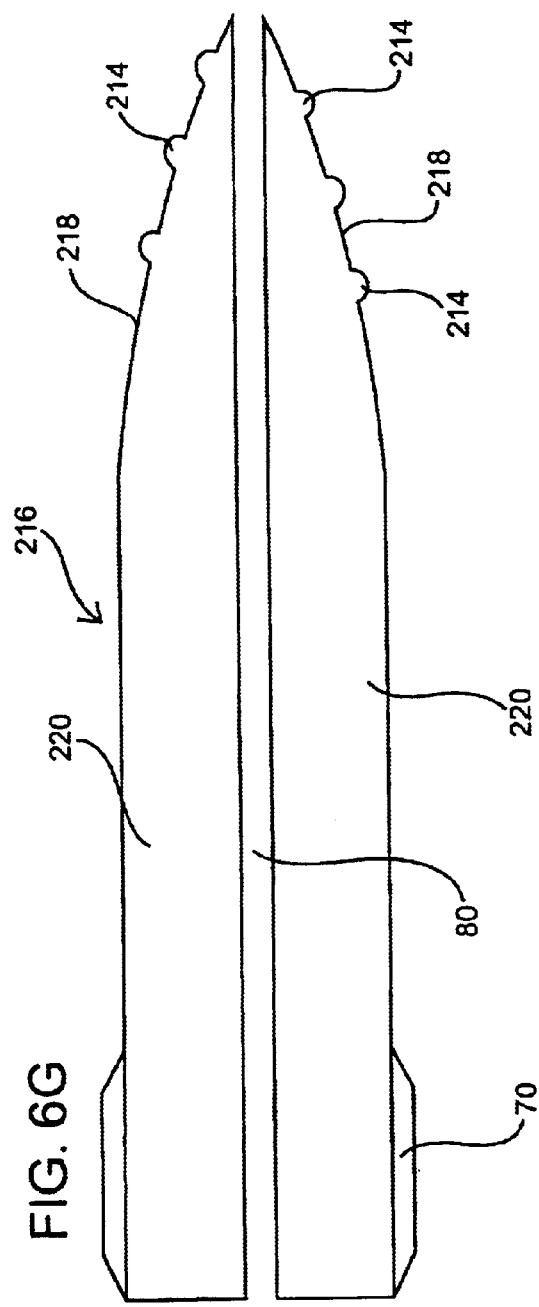

As opposed to cutting the tissue to prevent radial splitting, a modification to the dilator capable of minimizing the splitting is to include a screw-in mechanism in the dilator, as shown in FIGS. 6F and 6G. The screw-in, or rotating dilator 216 facilitates insertion by invoking rotation of the dilator through the opening in the host vessel wall. By rotating the dilator as the distal end taper is advanced, the opening expands at a slower rate and more uniform around the dilator preventing the splitting response associated with dramatic expansion of the opening. The rotating dilator 216 has a hub or handle 70, a lumen 80 to follow a guidewire or lumen, a main body 220 over which the deployment sheath resides and is advanced through the expanded opening, and a taper 218 to provide a smooth transition from the guidewire or needle (not shown) to the outer diameter of the main body 220. Threads 214 are incorporated on the distal end taper 218 and provide the surface to screw the dilator through the opening in the host vessel wall. The threads 214, as shown in FIGS. 6F and 6G, may be configured as radiused protrusions located along the distal end taper 218 and formed from the same material as the rest of the dilator during an injection molding, machining, or other manufacturing process. The threads may alternatively be formed as grooves created in the distal end taper 218 to provide an indentation for the opening through the host vessel wall to follow.

FIGS. 7A and 7B show an alternative dilating mechanism that also relieves the stress of the opening through the host vessel wall. This dilating mechanism 106 creates punches in the host vessel wall by removing a core of tissue prior to dilating the opening to the outer diameter necessary for inserting the deployment sheath. As stated above, a deployment sheath may be housed around the punching dilator 106 during creation of the opening. The ability to use the punching dilator 106 as the conduit for advancing the deployment sheath past the opening through the host vessel wall eliminates the need to swap a punch device for a dilator which may cause excess bleeding or require a second step for stopping or re-routing blood flow around the punched opening. The punching dilator 106 incorporates a movable distal section 108 which has a lumen 118 for a guidewire or needle to pass, a taper 112 to provide a smooth transition from the guidewire or needle to the outer diameter of the distal section 108, and a cutting element 110 for creating the punch through the host vessel wall. After the distal section 108 is advanced through the opening, the host vessel wall reside in the space between the proximal end of the distal section 108, which defines the cutting element 110, and the distal end of the proximal section 122. With the host vessel wall residing against the distal end of the proximal section 122, the distal section may be retracted by squeezing the distal section handle knob 116 towards the proximal section handle knob 124 thereby engaging the cutting element against the host vessel wall and cutting a hole of tissue out of the host vessel wall. After creating the punch, the cut tissue remains in the cavity 119 between the distal section 108 and the proximal section 122 and resides around the stylet 114 used to manipulate the distal section relative to the proximal section. This ensures the punched tissue will not become dislodged from the punching dilator and become an embolus. The punching dilator 106 maintains hemostasis through the opening after creating the punch and enables further expansion of the opening. The proximal section 122 has a taper 120 to provide a smooth transition from the distal section to the outer diameter of the proximal section. As stated earlier, after complete dilation of the opening has occurred, the deployment sheath (already contained around the punching dilator) may be advanced through the opening. Once the deployment sheath is positioned through the opening, the punching dilator may be removed leaving the deployment sheath as a conduit to insert the end-side fitting and bypass graft combination.

FIGS. 9A and 9B show an improvement to the splittable sheath which permits remote separation of the splittable deployment sheath into two separate but remotely attached components. This facilitates removal of the deployment sheath from the side of the bypass graft. After the bypass graft is attached at the anastomosis site using the end-side fittings as previously discussed, the scissors mechanism of the deployment sheath is actuated to separate the two halves of the splittable deployment sheath. This deployment sheath embodiment has a main tubing with a tapered distal end 94, a hub 92 with an integrated hemostatic valve 104, opposing grooves, splits, or perforations to permit separation of the sheath halves, and extensions that form a scissors mechanism to facilitate remote manipulation of the sheath halves. Each half of the hub 92 is connected to opposing legs 98 that intersect at a pivot 102 and extend to handles 100. The pivot 102 locks the two halves together but permits rotation of the opposing legs relative to each other. As the handles 100 are squeezes together, the halves of the sheath are urges apart providing a remote mechanism to separate the deployment sheath.

Another improvement to the deployment process applies to the splittable deployment system previously described or the sheathless deployment system described below and previously described. A suction plug may be used during the deployment to provide a working cavity 164 in which to deploy and secure the end-side fittings and attached bypass graft while minimizing blood leakage. FIGS. 13A and 13B show the cross-sectional profile of a suction plug 152 used to create a working cavity 164 when targeting small or medium sized host vessels (FIG. 13A), or large diameter host vessels (FIG. 13B). The suction plug may be fabricated so it can be split or be cut along at least one side for removal from around the side of the bypass graft once the end-side fitting is deployed into and secured to the host vessel. The suction plug 152 incorporates cells 162 that are interspersed throughout the flared end 168 of the suction plug. The cells 162 are interconnected through lumens 160 that route to a port 158 connected to the handle 166 of the suction plug. The port 158 is connected to a vacuum source capable of temporarily producing a vacuum within the cells capable of attaching the suction plug to a tissue surface. Alternatively, a deformable diaphragm (not shown) may replace the vacuum port and be depressed upon application of the suction plug to the surface such that releasing of the diaphragm creates a vacuum required to temporarily secure the suction plug to the tissue surface. A flapper valve (not shown) may also be incorporated in the suction plug to provide a mechanism to release the suction produced by the deformed diaphragm enabling removal of the suction plug from the tissue surface. This tissue surface may be the epicardium 150 surrounding a coronary artery (as shown in FIG. 13A) or the host vessel 2 (as shown in FIG. 13B). Once the suction plug is temporarily attached to the tissue surface, a cavity 164 is produced providing exposure to the host vessel but incorporating a hemostatic valve 154 to prevent excessive blood leakage during the surgical procedure. The cavity 164 is isolated from the suction cells 162 so the physician can open the valve and manipulate tissue exposed by the cavity without adversely affecting the temporary attachment of the suction plug to the tissue surface. The hemostatic valve 154 incorporates an opening to provide access to the host vessel exposed by the cavity.

The deployment system previously described may be inserted through the hemostatic valve 154 of the suction plug and into the host vessel. With the suction plug in place, the end-side fitting and bypass graft may be inserted through the deployment sheath and into the host vessel, and the support device may be secured to the base or stem of the fitting. The suction plug may also be used with the sheathless end-side fitting described below. In this case, the cavity provides a region to gain access into the host vessel, create longitudinal incisions or punches of tissue, deploy the end-side fittings through the opening, and secure the end-side fitting to the host vessel using a support device or other mechanism (e.g., adhesives, etc.). The suction plug also provides a stabilizing platform having a fixed distance between the valve 154 plane and the tissue surface; this enables automating vessel access, sheath introduction, and deployment of an end-side fitting. In this case, the suction plug provides a surface to mount the access, introduction, or fitting deployment component relative to the tissue surface and controllably rotate or advance the component relative to the tissue surface at known intervals.

FIG. 12 shows an improvement to the process of compressing the end-side fitting inside a loading sheath (previously described). The loading tool 142 atraumatically advances the end-side fitting and attached bypass graft inside the loading sheath and causes the petals of the end-side fitting to compress into a reduced diameter. A handle 144 is attached to the main body 148 of the loading tool and is used to manipulate the loading tool. The main body 148 has a cross-section that matches that of the base or stem of the end-side fitting. Extensions 146 to the main body 148 provide separations and are flared outward to push the base of the end-side fitting inside the loading sheath and provide spaces for the petals to compress forward into a reduced diameter. The loading sheath is placed around the bypass graft and base or stem of the end-side fitting and abuts the petals of the end-side fitting. The loading tool 142 is positioned against the distal end of the end-side fitting base or stem and is oriented such that the petals reside between the extensions 146. The loading tool is advanced inside the loading sheath causing the petals to compress forward into a reduced diameter and advances the base or stem of the end-side fitting sufficiently such that, when removed, the compressed end-side fitting remains inside the loading sheath with the petals in a reduced diameter.

Sheathless End-Side Fittings

As previously discussed in co-pending U.S. patent application Ser. No. 09/329,503 and co-pending Provisional Patent Application Serial No. 60/111,948, entitled "Bypass Graft Positioning and Securing Systems", filed Dec. 11, 1998, each of which is incorporated herein by reference in its entirety, end-side fitting embodiments having specific characteristics may be inserted through a small puncture without the need for a deployment sheath. FIGS. 1A to 1E and FIGS. 2A to 2D show dilating end-side fittings 10 that meet these requirements. The dilating end-side fittings 10 may incorporate a feature that enables following a guiding mechanism (e.g., guidewire, needle, or small dilator) directing the dilating end-side fitting into the host vessel interior and expand an opening through a host vessel wall.

In the embodiment shown in FIGS. 2A to 2C, an oval hole 20 in the leading petal 12 is adapted to follow a guidewire previously inserted through the host vessel wall and into the lumen, as shown in FIG. 2D. The guidewire 6 (or other mechanism), previously inserted through the host vessel wall, is inserted through the oval hole 20 such that when the end-side fitting is angled, the distal tip of the leading petal 12 follows the surface of the guidewire. This produces a smooth transition from the guidewire to the leading petal 12. As the end-side fitting is advanced, the leading petal expands the opening through the vessel wall.

The side petals 28, as shown in FIG. 2D, are maintained in a compressed configuration for the expansion of the opening and deployment through the host vessel wall. A guidewire 6 may be inserted through at least one of the spaces 26 incorporated in the side petals 28 and/or rear petal 14 such that compressing the petals inward using the guidewire holds the side petals 28 and the rear petal in a compressed configuration. The guidewire 6 further extends through the oval hole 20 in the leading petal 12, as discussed above. The compressed orientation of the side petals 28 and rear petal 14 enables dilating the opening through the host vessel wall facilitating advancement of the petals of the end-side fitting into the host vessel interior. When the petals of the end-side fitting are completely advanced through the opening, the mechanism (guidewire 6, hypotube, small dilator, or other device) used to maintain the side petals 28 and/or rear petal(s) 14 in a compressed configuration is removed enabling the petals of the fitting to expand towards their preformed configuration. Upon expansion, the petals engage the interior surface of the host vessel. Then a support device, previously discussed, is advanced over the stem or base 18 of the end-side fitting and is secured to maintain the position of the end-side fitting and prevent blood leakage. As shown in FIGS. 2A to 2D and previously discussed, relief cuts 24 may be incorporated in the end-side fitting to define extensions 30 which minimizes blood leakage and enable configuring the radius of curvature of the petals to maintain the maximum strain during compressing below the 8 percent limit characteristic of memory elastic materials.

As shown in FIGS. 3A to 3E, a thin wall sheath 34 having a height substantially smaller than the width or length may be used to maintain the side petals 28 and rear petal 14 in a compressed orientation during insertion through an opening into the host vessel. A remote extension 44 is attached to a handle (not shown) and permits remote manipulation of the thin wall sheath 34. As shown in FIGS. 3D and 3E, the interior surface of the thin wall sheath 34 matches the shape of the distal end of the compressed end-side fitting and provides an opening for the base or stem 18 of the fitting to emerge. The thin wall sheath resembles a dilator in that it provides a smooth surface and transition to expand the opening into the host vessel. The thin wall sheath provides at least one slot 40 on the top 36 of the sheath and at least one slot 42 on the bottom 38 of the sheath which permit separation of the thin wall sheath, once deployed, so the thin wall sheath 34 may be removed from around the compressed end-side fitting. The thin wall sheath 34 also has a minimal wall thickness to facilitate separation of the distal end of the thin wall sheath along the top slots 40 and bottom slots 42. Mechanisms previously discussed for splittable sheaths that hold the sheath in an intact configuration yet permit separation along the at least one side may be incorporated in top and bottom slots of this thin wall sheath 34 to enable remote separation of the thin wall sheath from around the end-side fitting. Removal of the thin wall sheath 34 allows the side petals 28 and the rear petal 14 to return towards their resting configuration such that the side petals 28 and rear petal 14 engage the interior surface and secure the end-side fitting (thus the attached bypass graft) to the host vessel.

FIGS. 1A to 1E show another dilating end-side fitting that does not require the use of a deployment sheath. As previously discussed, a guidewire may be inserted through the host vessel wall and into the host vessel interior, and the end-side fitting may or may not be capable of advancing over a guidewire (not shown). The leading petal 12 of the fitting provides a smooth transition from the opening into the host vessel along the leading petal of the end-side fitting to readily advance the leading petal 12 through the opening in the host vessel wall. The leading petal 12 has a smooth transition to the base of the end-side fitting to dilate the opening while the end-side fitting is advanced through the host vessel wall opening. The leading petal 12 also incorporates links 16 that define spaces 20 throughout the leading petal 12. The spaces 20 minimize the amount of foreign material exposed to blood flow and the links 16 permit compressing the leading petal into a reduced cross-section for insertion through an opening through the host vessel wall. The cross-section of the leading petal 12 (shown in FIG. 1C) is an arc having a radius of curvature to approximate the radius of curvature of the host vessel in the fittings resting configuration. Thus, when the end-side fitting is advanced completely inside the host vessel, the exterior surface of the leading petal contacts the interior surface of the host vessel and provides a structure to secure the fitting to the host vessel wall. The leading petal 12 may be slightly compressed together (by hand or using clamps) as shown in FIGS. 1D and 1E to produce a better transition for insertion through an opening in the host vessel wall; this also improves the transition from the leading petal to the base of the fitting and prevents scraping the side of the host vessel wall during insertion (especially when inserting the end-side fitting into a host vessel having a small or medium size diameter. Once the end-side fitting is advanced until the base 18 of the fitting resides approximate the opening through the host vessel wall, the rear petal 14 must be advanced through the opening. The rear petal 14 may be deflected towards the base 18 of the end-side fitting using the guidewire, clamp, or due to the force exerted by the host vessel wall as the proximal end of the end-side fitting is advanced through the host vessel wall. This rear petal is designed so it is capable of bending towards the base of the fitting but is unable to readily deflect towards the leading petal 12. Alternatively, as shown in FIGS. 2A to 2D, the rear petal may be fabricated such that it readily deflects forward toward the leading petal. This is especially useful when a guidewire may be used to compress the rear petal toward the leading petal while inserting the end-side fitting through an opening into the host vessel wall, as previously discussed. The rear petal 14 further anchors the end-side fitting inside the host vessel. In the preferred embodiment, the length of the rear petal 14 is less than the diameter of the host vessel and is positioned so the rear petal 14 may be advanced through the opening without the leading petal 12 or base of the fitting having to deform the posterior surface of the host vessel. Once positioned entirely through the host vessel wall, a support device is used to lock the end-side fitting inside the host vessel and prevent blood leakage between the opening through the host vessel wall and the base 18 of the end-side fitting.

To facilitate deployment of the dilating end-side fitting, the rear petal may be fabricated as a separate component from the fitting, as shown in FIGS. 4A to 4D. This separate rear petal 50 is capable of locking to the distal leading component after the fitting is positioned through an opening in the host vessel wall and the rear petal is positioned appropriately. As shown in FIG. 4A, the stem or base of the fitting incorporates at least one slot 48 for the rear petal to slide. The end-side fitting also incorporates a leading petal 12, side petals 46 that may or may not compress during insertion, holes 20 and 26 through the leading and side petals, relief cuts defining extensions 30 that enhance hemostasis at the anastomosis, and a base or stem 18 for securing the bypass graft and maintaining the patency of the opening through the host vessel wall. Once the leading petal 12 and the side petals 46 of the fitting are inserting into the host vessel interior, the rear petal is advanced through the slot 48 in the base or stem 18 of the fitting and is secured to the base or stem of the fitting using a locking mechanism 52. The rear petal may also include holes to improve flexibility of the petal and promote cellular growth.

As a result of the sheathless deployment processes discussed above, these end-side fittings may be fabricated using any biocompatible material (e.g., nickel titanium, PET, PTFE, urethane, silicone, polyester, etc.) or composite of materials and manufacturing processes such as injection molding, blow molding, or dipping.

I claim:

1. An end-side anastomosis system including a fitting comprising:

a base for attachment to a graft, said base being configured to form a seal with an opening in a host vessel wall;

a leading petal having a cross-section with a radius of curvature approximating a radius of curvature of the host vessel, said leading petal being configured to dilate the host vessel wall opening while advancing said fitting through the opening, said fitting including links defining spaces throughout said leading petal; and a rear petal, said rear petal being deflectable to be advanced through the host vessel opening.

2. The system of claim 1, wherein said rear petal is deflectable toward said leading petal.

3. The system of claim 1, wherein said rear petal comprises a separate component from a portion of said fitting including said base and said leading petal.

4. The system of claim 3, wherein said base includes a slot for receiving said separate rear petal.

5. The system of claim 3, wherein said separate rear petal includes a locking mechanism for attachment of said separate rear petal to said base.

6. The system of claim 5, wherein said locking mechanism includes a hooked portion.

7. The system of claim 1, wherein said fitting includes side petals between said leading petal and said rear petal.

8. The system of claim 1, wherein at least one petal defines at least one space therethrough.

9. The system of claim 1, wherein said fitting includes extensions around said base to provide improved hemostasis.

10. The system of claim 1, further including a deployment sheath for housing said fitting when compressed, said sheath being configured to serve as a dilator and being adapted for removal from said fitting once said fitting is in place.

* * * * *